(12) United States Patent
Bigio et al.

(10) Patent No.: US 9,463,250 B2
(45) Date of Patent: Oct. 11, 2016

(54) CONJUGATE PURIFICATION

(75) Inventors: Massimo Bigio, Siena (IT); Giovanni Averani, Siena (IT); Francesco Norelli, Siena (IT); Francesco Berti, Siena (IT); Cinzia Bellucci, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 594 days.

(21) Appl. No.: 12/669,464

(22) PCT Filed: Jul. 17, 2008

(86) PCT No.: PCT/IB2008/002690
§ 371 (c)(1),
(2), (4) Date: Jun. 9, 2010

(87) PCT Pub. No.: WO2009/010877
PCT Pub. Date: Jan. 22, 2009

(65) Prior Publication Data
US 2010/0239600 A1 Sep. 23, 2010

(30) Foreign Application Priority Data

Jul. 17, 2007 (GB) .................................. 0713880.3

(51) Int. Cl.
| | | |
|---|---|---|
| *A61K 39/385* | (2006.01) | |
| *C07K 1/14* | (2006.01) | |
| *C07K 1/16* | (2006.01) | |
| *A61K 47/48* | (2006.01) | |
| *A61K 39/09* | (2006.01) | |
| *B01D 15/38* | (2006.01) | |
| *B01J 20/04* | (2006.01) | |
| *A61K 39/095* | (2006.01) | |
| *A61K 39/085* | (2006.01) | |
| *A61K 39/112* | (2006.01) | |
| *A61K 39/02* | (2006.01) | |
| *A61K 39/104* | (2006.01) | |
| *A61K 39/00* | (2006.01) | |

(52) U.S. Cl.
CPC ....... *A61K 47/48261* (2013.01); *A61K 39/092* (2013.01); *A61K 47/4833* (2013.01); *A61K 47/48246* (2013.01); *A61K 47/48269* (2013.01); *B01D 15/3847* (2013.01); *B01J 20/048* (2013.01); *C07K 1/165* (2013.01); *A61K 39/0275* (2013.01); *A61K 39/085* (2013.01); *A61K 39/095* (2013.01); *A61K 39/104* (2013.01); *A61K 39/107* (2013.01); *A61K 2039/6037* (2013.01)

(58) Field of Classification Search
CPC .................. A61K 2039/6037; A61K 39/092; A61K 47/48246; A61K 47/48261; A61K 47/48269; A61K 47/4833; A61K 2039/55505; A61K 2039/70; A61K 39/00; A61K 39/0017; A61K 39/05; A61K 39/08; A61K 39/095; A61K 39/099
See application file for complete search history.

(56) References Cited

U.S. PATENT DOCUMENTS

| | | | |
|---|---|---|---|
| 4,057,685 A | 11/1977 | McIntire | |
| 4,356,170 A | 10/1982 | Jennings et al. | |
| 4,459,286 A | 7/1984 | Hilleman et al. | |
| 4,663,160 A | 5/1987 | Tsay et al. | |
| 4,673,574 A | 6/1987 | Anderson | |
| 4,695,624 A | 9/1987 | Marburg et al. | |
| 4,761,283 A | 8/1988 | Anderson | |
| 4,808,700 A | 2/1989 | Anderson et al. | |
| 4,882,317 A | 11/1989 | Marburg et al. | |
| 4,965,338 A | 10/1990 | Tabankia et al. | |
| 5,011,828 A | 4/1991 | Goodman et al. | |
| 5,057,540 A | 10/1991 | Kensil et al. | |
| 5,658,731 A | 8/1997 | Sproat et al. | |
| 5,916,588 A | 6/1999 | Popescu et al. | |
| 6,090,406 A | 7/2000 | Popescu et al. | |
| 6,146,902 A | 11/2000 | McMaster | |
| 6,207,646 B1 | 3/2001 | Krieg et al. | |
| 6,231,864 B1* | 5/2001 | Birkett ........................ | 424/189.1 |
| 6,239,116 B1 | 5/2001 | Krieg et al. | |
| 6,284,250 B1 | 9/2001 | Lees et al. | |
| 6,299,884 B1 | 10/2001 | Van Nest et al. | |
| 6,429,199 B1 | 8/2002 | Krieg et al. | |
| 6,451,325 B1 | 9/2002 | Van Nest et al. | |
| 6,586,409 B1 | 7/2003 | Wheeler | |
| 6,605,617 B2 | 8/2003 | Renhowe et al. | |
| 6,699,703 B1 | 3/2004 | Doucette-Stamm et al. | |
| 6,800,744 B1 | 10/2004 | Doucette-Stamm et al. | |
| 6,924,271 B2 | 8/2005 | Averett et al. | |
| 2005/0070556 A1 | 3/2005 | Averett et al. | |
| 2005/0215517 A1 | 9/2005 | Rossignol et al. | |
| 2006/0228380 A1* | 10/2006 | Hausdorff et al. ......... | 424/244.1 |

(Continued)

FOREIGN PATENT DOCUMENTS

| | | |
|---|---|---|
| EP | 0109942 B1 | 5/1984 |
| EP | 0208375 B1 | 1/1987 |

(Continued)

OTHER PUBLICATIONS

Dona et al. Clin. Chim. Acta. 108: 301-307, 1980.*

(Continued)

*Primary Examiner* — S. Devi
(74) *Attorney, Agent, or Firm* — Morrison & Foerster LLP

(57) ABSTRACT

This application relates to methods for the purification of saccharide antigen-carrier protein conjugates. In particular, the invention provides a method for purifying saccharide antigen-carrier protein conjugates from free carrier protein, such as CRM1 97, using hydroxyapatite. The invention further relates to methods of preparing vaccines, using this method.

17 Claims, 8 Drawing Sheets

(56) References Cited

U.S. PATENT DOCUMENTS

| | | | | |
|---|---|---|---|---|
| 2008/0199909 | A1* | 8/2008 | Buechler et al. | 435/69.4 |
| 2011/0206692 | A1* | 8/2011 | Maione et al. | 424/164.1 |

FOREIGN PATENT DOCUMENTS

| | | | |
|---|---|---|---|
| EP | 0372501 | A2 | 6/1990 |
| EP | 0378881 | B1 | 7/1990 |
| EP | 0427347 | B1 | 5/1991 |
| EP | 0471177 | B1 | 2/1992 |
| EP | 0594610 | B1 | 5/1994 |
| EP | 0626169 | B1 | 11/1994 |
| EP | 0689454 | B1 | 1/1996 |
| EP | 0835318 | A2 | 1/1997 |
| EP | 0735898 | B1 | 3/1999 |
| EP | 0761231 | B1 | 1/2000 |
| WO | WO-90/14837 | A1 | 12/1990 |
| WO | WO-91/01146 | A1 | 2/1991 |
| WO | WO-93/17712 | A2 | 9/1993 |
| WO | WO-94/00153 | A1 | 1/1994 |
| WO | WO-94/03208 | A1 | 2/1994 |
| WO | WO-94/06467 | A1 | 3/1994 |
| WO | WO-95/08348 | A1 | 3/1995 |
| WO | WO-95/17211 | A1 | 6/1995 |
| WO | WO-96/11711 | A1 | 4/1996 |
| WO | WO-96/29412 | A1 | 9/1996 |
| WO | WO-96/33739 | A1 | 10/1996 |
| WO | WO-97/37026 | A1 | 10/1997 |
| WO | WO-97/43303 | A1 | 11/1997 |
| WO | WO-98/18930 | A2 | 5/1998 |
| WO | WO-98/18931 | A2 | 5/1998 |
| WO | WO-98/20734 | A1 | 5/1998 |
| WO | WO-98/40100 | A1 | 9/1998 |
| WO | WO-98/42375 | A1 | 10/1998 |
| WO | WO-98/42721 | A1 | 10/1998 |
| WO | WO-98/57659 | A1 | 12/1998 |
| WO | WO-98/58668 | A2 | 12/1998 |
| WO | WO-99/11241 | A1 | 3/1999 |
| WO | WO-99/24578 | A2 | 5/1999 |
| WO | WO-99/27960 | A1 | 6/1999 |
| WO | WO-99/28475 | A2 | 6/1999 |
| WO | WO-99/36544 | A2 | 7/1999 |
| WO | WO-99/40936 | A1 | 8/1999 |
| WO | WO-99/44636 | A2 | 9/1999 |
| WO | WO-99/52549 | A1 | 10/1999 |
| WO | WO-99/55730 | A2 | 11/1999 |
| WO | WO-99/57280 | A2 | 11/1999 |
| WO | WO-99/58562 | A1 | 11/1999 |
| WO | WO-99/62923 | A2 | 12/1999 |
| WO | WO-00/07621 | A2 | 2/2000 |
| WO | WO-00/10599 | A2 | 3/2000 |
| WO | WO-00/22430 | A2 | 4/2000 |
| WO | WO-00/23105 | A2 | 4/2000 |
| WO | WO-00/37494 | A2 | 6/2000 |
| WO | WO-00/38711 | A2 | 7/2000 |
| WO | WO-00/56360 | A2 | 9/2000 |
| WO | WO-00/61761 | A1 | 10/2000 |
| WO | WO-00/66791 | A1 | 11/2000 |
| WO | WO-01/21152 | A1 | 3/2001 |
| WO | WO-01/21207 | A2 | 3/2001 |
| WO | WO-01/30390 | A2 | 5/2001 |
| WO | WO-01/52885 | A1 | 7/2001 |
| WO | WO-01/64920 | A2 | 9/2001 |
| WO | WO-01/64922 | A2 | 9/2001 |
| WO | WO-01/72337 | A1 | 10/2001 |
| WO | WO-01/95935 | A1 | 12/2001 |
| WO | WO-02/18383 | A2 | 3/2002 |
| WO | WO-02/18595 | A2 | 3/2002 |
| WO | WO-02/22167 | A2 | 3/2002 |
| WO | WO-02/26757 | A2 | 4/2002 |
| WO | WO-02/34771 | A2 | 5/2002 |
| WO | WO-02/072012 | A2 | 9/2002 |
| WO | WO-02/079243 | A2 | 10/2002 |
| WO | WO-02/091998 | A2 | 11/2002 |
| WO | WO-02/094851 | A2 | 11/2002 |
| WO | WO-03/007985 | A2 | 1/2003 |
| WO | WO-03/009869 | A1 | 2/2003 |
| WO | WO-03/011223 | A2 | 2/2003 |
| WO | WO-03/020756 | A2 | 3/2003 |
| WO | WO-03/024480 | A2 | 3/2003 |
| WO | WO-03/024481 | A2 | 3/2003 |
| WO | WO-03/035836 | A2 | 5/2003 |
| WO | WO-03/049762 | A2 | 6/2003 |
| WO | WO-03/068811 | A2 | 8/2003 |
| WO | WO-03/080678 | A1 | 10/2003 |
| WO | WO-03/082272 | A1 | 10/2003 |
| WO | WO-03/093306 | A2 | 11/2003 |
| WO | WO-2004/018455 | A1 | 3/2004 |
| WO | WO-2004/032958 | A1 | 4/2004 |
| WO | WO-2004/041157 | A2 | 5/2004 |
| WO | WO-2004/048404 | A2 | 6/2004 |
| WO | WO-2004/060308 | A2 | 7/2004 |
| WO | WO-2004/064715 | A2 | 8/2004 |
| WO | WO-2004/064759 | A2 | 8/2004 |
| WO | WO-2004/087153 | A2 | 10/2004 |
| WO | WO-2005/002619 | A2 | 1/2005 |
| WO | WO-2005/032582 | A2 | 4/2005 |
| WO | WO-2005/033148 | A1 | 4/2005 |
| WO | WO-2005/090985 | A | 9/2005 |
| WO | WO-2006/002422 | A2 | 1/2006 |
| WO | WO-2006/050341 | A2 | 5/2006 |
| WO | WO-2006/067632 | A2 | 6/2006 |
| WO | WO-2006/082527 | A2 | 8/2006 |
| WO | WO-2006/082530 | A2 | 8/2006 |
| WO | WO-2006/110381 | A | 10/2006 |
| WO | WO-2007/000341 | A2 | 1/2007 |
| WO | WO-2007/000342 | A2 | 1/2007 |

OTHER PUBLICATIONS

Joshi et al. Microsc. Microanal. 11, Suppl. 2, 1176-1177, 2005.*
Chapter 9.4, Yersinia enterocolitica. In: 'Ensuring Global Food Safety: Exploring Global Harmonization'. (Ed) Christine Boisrobert et al., pp. 157-160, First Edition, Academic Press, Chapter 9.4, 2010.*
Alexander et al. (2000) *J Immunol* 164:1625-1633.
Allison & Byars (1992) *Res Immunol* 143:519-25.
Anderson (1983) *Infect Immun* 39(1):233-238.
Anderson (2001) *Vaccine* 19(Suppl 1):559-65.
Anderson et al. (1985) *J Clin Invest* 76(1):52-59.
Andrianov et al. (1998) *Biomaterials* 19:109-115.
Balmer et al. (2002) *J Med Microbiol* 51:717-722.
Baraldo et al. (2004) *Infect Immun* 72(8):4884-7.
Barr et al. (1998) *Adv Drug Deliv Rev* 32:247-271.
Beignon et al. (2002) *Infect Immun* 70:3012-3019.
Bell (2000) *Pediatr Infect Dis J* 19:1187-1188.
Bhagat et al. (2003) *BBRC* 300:853-861.
Bjune et al. (1991) *Lancet* 338(8775):1093-96.
Blackwell et al. (2003) *J Immunol* 170:4061-4068.
Cooper (1995) *Pharm Biotechnol* 6:559-80.
Costantino et al. (1992) *Vaccine* 10:691-698.
Costantino et al. (1999) *Vaccine* 17:1251-1263.
Crowe (1995) *Vaccine* 13:415-421.
Dale (1999) *Infect Dis Clin North Am* 13:227-243.
Dale (1999) *Vaccine* 17:193-200.
Dale (Jul. 1996) *Vaccine* 14(10): 944-948.
Domenighini et at. (1995) *Mol Microbiol* 15:1165-1167.
Dona, V et al. (Dec. 8, 1980) *Clinica Chimica Acta* 108(2):301-307.
Evans et al. (2003) *Expert Rev Vaccines* 2:219-229.
Falugi et al. (2001) *Eur J Immunol* 31 :3816-3824.
Ferretti et al. (2001) *PNAS USA* 98:4658-4663.
Frey et al. (2003) *Vaccine* 21:4234-4237.
Fukasawa et al. (1999) *Vaccine* 17:2951-2958.
Gerber et al. (2001) *Virol* 75:4752-4760.
Gerlich et al. (1990) *Vaccine* 8(Suppl):79-80 & S93-S94.
Geyer et al. (1979) *Med Microbiol Immunol* 165:271-288.
Gluck et al. (2002) *Vaccine* 20:B10-B16.
Gustafsson et al. (1996) *N Engl. J. Med.* 334:349-355.
Hariharan et al. (1995) *Cancer Res* 55:3486-9.
International Search Report mailed Sep. 30, 2009, for PCT Application No. PCT/IB2008/002690 filed Jul. 17, 2008, 5 pages.

(56) References Cited

OTHER PUBLICATIONS

Iwarson (1995) *APMIS* 103:321-326.
Jedrzejas (2001) *Microbiol Mol Biol Rev* 65:187-207.
Johnson et al. (1999) *Bioorg Med Chem Lett* 9:2273-2278.
Johnstone (Nov. 2004) *J Gen Virol.* 85(11):3229-3238.
Jones (2003) *Curr Opin Investig Drugs* 4:214-218.
Kahn (2000) *Curr Opin Pediatr* 12:257-262.
Kandimalla et al. (2003) *Biochem Soc Trans* 31(3):654-658.
Kandimalla et al. (2003) *Nuc Acids Res* 31:2393-2400.
Kandimalla et at. (2003) *BBRC* 306:948-953.
Krieg (2002) *Trends Immunol* 23:64-65.
Krieg (2003) *Nature Medicine* 9:831-835.
Kuo et al. (1995) *Infect Immun* 63:2706-13.
Kuroda et al. (2001) *Lancet* 357(9264):1225-1240.
Lees et al. (1996) *Vaccine* 14:190-198.
Lei et al. (2000) *Dev Biol* (Basel) 103:259-264.
Lenz et al. (2001) *J Immunol* 166:5346-5355.
Lillard et al. (Feb. 1, 2003) *Blood* 101(3):807-814.
Matsui M. et al. (2004) *J. Virol* 78: 9093-9104.
McCluskie et al. (2002) *FEMS Immun Med Microbiol* 32:179-185.
McMichael (2000) *Vaccine* 19(Suppl 1):S101-107.
Meraldi et al. (2003) *Vaccine* 21:2485-2491.
Niikura et al. (2002) *Virology* 293:273-280.
O'Hagan, Ed. (Apr. 15, 2000). "Vaccine Adjuvants: Preparation Methods and Research Protocols," vol. *42 of Methods in Molecular Medicine.* ISBN: 1-59259-083-7.
Pajak et al. (2003) *Vaccine* 21:836-842.
Paoletti et al., (1990) *J Biol Chem* 265:18278-18283.
Partidos et at. (1999) *Immunol Lett* 67:209-216.
Payne et al. (1998) *Adv Drug Delivery Review* 31:185-196.
Peltola (2000) *Clin Microbiol Rev* 13:302-317.
Peppoloni et al. (2003) *Expert Rev Vaccines* 2:285-293.
Pine et al. (2002) *J Control Release* 85:263-270.
Pinto et al. (2003) *J Infect Dis* 188:327-338.
Pizza et al. (2000) *Science* 287:1816-1820.
Pizza et al. (2001) *Vaccine* 19:2534-2541.
Pizza et at. (2000) *Int J Med Microbiol* 290:455-461.
Plante et al. (2000) *J Infectious Disease* 182:848-855.
Plotkin et al., Eds. (2003). *Vaccine, Fourth Edition*, W B Saunders Co, ISBN 0-7216-9688-0.
Podda (2001) *Vaccine* 19:2673-2680.
Porro et al. (1985). *Mol. Immunol.* 22:907-919.
Powell & Newman, Eds. (1995). *Vaccine Design: The Subunit & Adjuvant Approach*, Plenum Pub Corp., ISBN: 030644867X.
Price et al. (2004) *Infection and Immunity* 72(1):277-283.
Rappuoli et al. (1991) *TIBTECH* 9:232-238.
Ravenscroft et al. (1999) *Vaccine* 17:2802-2816.
Rosenqvist et al. (1998) *Dev. Biol. Stand.* 92:323-333.
Ruan et al. (1990) *J Immunol* 145:3379-3384.
Rubin (2000) *Pediatr Clin North Am* 47:269-285.
Ryan et al. (1999) *Infect Immun* 67:6270-6280.
Scharton-Kersten et al. (2000) *Infect Immun* 68:5306-5313.
Schuchat (1999) *Lancet* 353(9146):51-56.
Shen et al. (Nov. 22, 2000) *Vaccine* 19(7-8):850-861.
Signorelli & Hadden (2003) *Int Immunopharmacol* 3(8):1177-1186.
Singh et al. (2001) *J Cont Release* 70:267-276.
Sjolan Der et al. (1998) *Advanced Drug Delivery Reviews* 32:321-338.
Stanley (2002) *Clin Exp Dermatol* 27:571-577.
Tettelin et al. (2000) *Science* 287:1809-1815.
U.S. Appl. No. 61/008,941, entitled "Fermentation Processes for Cultivating Streptococci and Purification Processes for Obtaining CPS Therefrom" filed Dec. 20, 2007.
Watson (2000) *Pediatr Infect Dis J* 19:331-332.
Wessels et al. (1989) *Infect Immun* 57:1089-1094.
Wessels et al. (1990) *J Clin Invest* 86(5):1428-1433.
Wessels et al., (1995) *J Infect Dis* 171:879-84.
Wong et al. (2003) *J Clin Pharmacol* 43(7):735-742.
Wuorimaa & Kayhty (2002) *Scand J Immunol* 56:111-129.
Zhu et al. (2004). *Vaccine* 23:78-83.
Gagnon (1998). "An Enigma Unmasked: How Hydroxyapatite Works, and How to Make It Work for You," Retrieved Apr. 8, 2015 from <http://www.validated.com/revalbio/pdffiles/hxyapt.pdf >.

\* cited by examiner

Figure 2

| | |
|---|---|
| Ia | [→4)-β-D-Glcp-(1→4)-β-D-Galp-(1→]$_n$<br>3<br>↑<br>1<br>β-D-GlcpNAc<br>4<br>↑<br>1<br>β-D-Galp<br>3<br>↑<br>2<br>α-D-NeupNAc |
| Ib | [→4)-β-D-Glcp-(1→4)-β-D-Galp-(1→]$_n$<br>3<br>↑<br>1<br>β-D-GlcpNAc<br>3<br>↑<br>1<br>β-D-Galp<br>3<br>↑<br>2<br>α-D-NeupNAc |
| II | [→4)-β-D-GlcpNAc-(1→3)-β-D-Galp-(1→4)-β-D-Glcp-(1→3)-β-D-Glcp-(1→2)-β-D-Galp-(1→]$_n$<br>6                                                  3<br>↑                                                    ↑<br>1                                                    2<br>β-D-Galp                                  α-D-NeupNAc |
| III | →4)-β-D-Glcp-(1→6)-β-D-GlcpNAc-(1→3)-β-D-Galp-(1→<br>4<br>↑<br>1<br>β-D-Galp<br>3<br>↑<br>2<br>α-D-NeupNAc |
| V | →4)-α-D-Glcp-(1→4)-β-D-Galp-(1→4)-β-D-Glcp-(1→<br>6               3<br>↑               ↑<br>1               1<br>β-D-GlcpNAc   β-D-Glcp<br>4<br>↑<br>1<br>β-D-Galp<br>3<br>↑<br>2<br>α-D-NeupNAc |

CONJUGATE PURIFICATION

CROSS REFERENCE TO RELATED APPLICATIONS

This application is a U.S. National Phase patent application of International Application No. PCT/IB2008/002690, with an international filing date of Jul. 17, 2008, which claims priority to Great Britain 0713880.3, filed on Jul. 17, 2007, all of which are incorporated herein by reference in their entirety.

This application claims priority from UK patent application 0713880.3, the full contents of which are incorporated by reference herein.

TECHNICAL FIELD

This invention is in the field of vaccines and relates to a new method for purifying saccharide antigen-carrier protein conjugates.

BACKGROUND ART

In the last 20 years, conjugate vaccines, comprising bacterial capsular polysaccharides conjugated to protein carriers have developed. Examples include the *Haemophilus influenzae* type b (Hib) conjugate vaccine [1] as well as conjugate vaccines against *Streptococcus pneumoniae* [2] and serogroup C *Neisseria meningitidis* (MenC) [3].

The carrier proteins used in licensed vaccines include tetanus toxoid (TT), diphtheria toxoid (DT), the nontoxic CRM197 mutant of diptheria toxin, and the outer membrane protein complex from group B *N. meningitidis*. Ideally, a carrier protein induces strong helper effect to a conjugated B-cell epitope (e.g. polysaccharide) without inducing an antibody response against itself. The use of universal epitopes, which are immunogenic in the context of most major histocompatability complex class II molecules, is one approach towards this goal [4]. Such epitopes have been identified within TT and other proteins. Alternatively, multi-epitope carrier proteins may be used, such as those described in reference 5.

Once a saccharide antigen has been conjugated to a carrier protein, the reaction mixture should be purified to remove free carrier protein that has no saccharide antigen conjugated thereto and unconjugated saccharide.

Various methods for the purification of free and conjugated carrier protein are known in the art, including hydrophobic chromatography, tangential ultrafiltration, diafiltration etc. [see also refs. 6 & 7, etc.]. However, these methods suffer from various drawbacks. For example, reference 8 proposes the use of gel filtration to purify GBS conjugates. However, this method requires a large volume of gel filtration matrix and is difficult to apply at a manufacturing scale. An alternative method that involves ultrafiltration, for example using tangential flow diafiltration with a 100 KDa membrane, is not effective unless the saccharide antigen is of a suitably high molecular weight and is thus not suitable for GBS serotype III conjugates or other conjugates where the saccharide antigen is <100 kDa. In addition, ultrafiltration can result in a low yield and stress the conjugate.

It is therefore the object of the invention to provide an improved method of purifying saccharide antigen-carrier protein conjugates from impurities such as unconjugated carrier protein and unconjugated saccharide.

DISCLOSURE OF THE INVENTION

It has been discovered that conjugation of saccharide antigens to carrier proteins can alter the carrier proteins' binding affinity for hydroxyapatite. Thus, in a mixture comprising saccharide antigen-carrier protein conjugates, unconjugated carrier protein and other proteins, the contaminant/unconjugated proteins bind to hydroxyapatite while saccharide antigen-carrier protein conjugates do not substantially bind.

Thus, the invention provides a method of purifying saccharide antigen-carrier protein conjugates from a mixture, comprising contacting said mixture with hydroxyapatite and collecting the free saccharide antigen-carrier protein conjugates. The unbound carrier protein may optionally be eluted from the hydroxyapatite and re-used in a conjugation reaction, assayed or discarded.

The mixture may comprise saccharide antigen-carrier protein conjugates and unconjugated protein. However, the mixture may also be contaminated with other proteins. The method of the invention allows any contaminating proteins to be removed, thus providing purified saccharide antigen-carrier protein conjugates.

The invention further provides a method of preparing a pharmaceutical composition, comprising the steps of i) contacting a mixture comprising saccharide antigen-carrier protein conjugates and free carrier protein with hydroxyapatite, ii) collecting the free saccharide antigen-carrier protein conjugates, and iii) mixing said saccharide antigen-carrier protein conjugates obtained in step ii) with a pharmaceutically acceptable diluent or carrier. The invention also provides the compositions prepared by said method.

Carrier Protein

The carrier protein may be selected from those known in the art, such as, tetanus toxoid (TT), diphtheria toxoid (DT), or derivatives thereof such as the nontoxic CRM197 mutant of diphtheria toxin [9-11]. Other suitable carrier proteins include the *N. meningitidis* outer membrane protein [12], synthetic peptides [13,14], heat shock proteins [15,16], pertussis proteins [17,18], cytokines [19], lymphokines [19], hormones [19], growth factors [19], artificial proteins comprising multiple human CD4[+] T cell epitopes from various pathogen-derived antigens [20] such as N19 [21], protein D from *H. influenzae* [22-24], pneumolysin [25], pneumococcal surface protein PspA [26], iron-uptake proteins [27], toxin A or B from *C. difficile* [28], etc. However, any carrier protein may be used provided that it binds to hydroxyapatite.

Diphtheria toxoid (DT), tetanus toxoid (TT) and CRM197 are the main carriers currently in use in pediatric vaccines e.g. the HIBERIX™ and MENITORIX™ conjugates from GSK use TT as the carrier, the HIBTITER™ product uses CRM197, the pneumococcal conjugates in PREVENAR™ use CRM197, the MENJUGATE™ and MENINGITEC™ products use CRM197, and NEISVAC-C™ uses TT.

Alternatively, the carrier protein may be a multi-epitope carrier protein such as those described in reference 5. Such multi-epitope carriers include N19.

Preferably the carrier protein used in the invention is CRM197.

Saccharide Antigens

Preferably, the saccharide antigen conjugated to the carrier protein in a composition purified by the invention is a bacterial saccharide and in particular a bacterial capsular saccharide. LPS or LOS may also be used as the antigen.

Preferably, the saccharide antigen according to the invention has a molecular weight of 5 KDa or more, more preferably 8 KDa or more (i.e. 10, 15, 20, 25, 30, 35, 40, 45, 50, 60, 70, 80, 90, 100, 125, 150, 175, 200, 225, 250 KDa or more).

Examples of bacterial capsular saccharides which may be included in the compositions of the invention include capsular saccharides from *Neisseria meningitidis* (serogroups A, B, C, W135 and/or Y), *Streptococcus pneumoniae* (serotypes 1, 2, 3, 4, 5, 6B, 7F, 8, 9N, 9V, 10A, 11A, 12F, 14, 15B, 17F, 18C, 19A, 19F, 20, 22F, 23F and 33F, particularly 4, 6B, 9V, 14, 18C, 19F and/or 23F), *Streptococcus agalactiae* (types Ia, Ib, II, III, IV, V, VI, VII, and/or VIII, such as the saccharide antigens disclosed in references 29-32), *Haemophilus influenzae* (typeable strains: a, b, c, d, e and/or f), *Pseudomonas aeruginosa*, *Staphylococcus aureus* (from, for example, serotypes 5 and 8), *Enterococcus faecalis* or *E. faecium* (trisaccharide repeats), *Yersinia enterocolitica, Vibrio cholerae, Salmonella typhi, Klebsiella* spp., etc. Other saccharides which may be included in the compositions of the invention include glucans (e.g. fungal glucans, such as those in *Candida albicans*), and fungal capsular saccharides e.g. from the capsule of *Cryptococcus neoformans*. Another saccharide which may be included is the *Streptococcus pyogenes* group-specific antigen (GAS carbohydrate).

Examples of LPS and LOS include LPS isolated from PA01, O5 serotype of *Pseudomonas aeruginosa*.

The *N. meningitidis* serogroup A (MenA) capsule is a homopolymer of ($\alpha$1→6)-linked N-acetyl-D-mannosamine-1-phosphate, with partial O-acetylation in the C3 and C4 positions. The *N. meningitidis* serogroup B (MenB) capsule is a homopolymer of ($\alpha$2→8)-linked sialic acid. The *N. meningitidis* serogroup C (MenC) capsular saccharide is a homopolymer of ($\alpha$2→9) linked sialic acid, with variable O-acetylation at positions 7 and/or 8. The *N. meningitidis* serogroup W135 saccharide is a polymer having sialic acid-galactose disaccharide units [→4)-D-Neup5Ac(7/9OAc)-$\alpha$-(2→6)-D-Gal-$\alpha$-(1→]. It has variable O-acetylation at the 7 and 9 positions of the sialic acid [33]. The *N. meningitidis* serogroup Y saccharide is similar to the serogroup W135 saccharide, except that the disaccharide repeating unit includes glucose instead of galactose [→4)-D-Neup5Ac(7/9OAc)-$\alpha$-(2→6)-D-Glc-$\alpha$-(1→]. It also has variable O-acetylation at positions 7 and 9 of the sialic acid.

Preferably, the saccharide antigens are from GBS, serotypes Ia, Ib and/or III. Also preferred are saccharide antigens from other GBS serotypes, e.g. serotypes II, IV, V, VI, VII and/or VIII. In particular, the saccharide antigen may be the *Streptococcus agalactiae* capsular saccharide from these serotypes, which is covalently linked to GlcNAc residues in the bacterium's peptidoglycan backbone. The capsular polysaccharides of different serotypes are chemically related, but are antigenically very different. All GBS capsular polysaccharides share the following trisaccharide core:

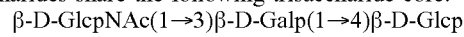

β-D-GlcpNAc(1→3)β-D-Galp(1→4)β-D-Glcp

The various GBS serotypes differ by the way in which this core is modified. The difference between serotypes Ia and III, for instance, arises from the use of either the GlcNAc (Ia) or the Gal (III) in this core for linking consecutive trisaccharide cores (FIG. 1). Serotypes Ia and Ib both have a [$\alpha$-D-NeupNAc(2→3)β-D-Galp-(1→] disaccharide linked to the GlcNAc in the core, but the linkage is either 1→4 (Ia) or 1→3 (Ib).

GBS-related disease arises primarily from serotypes Ia, Ib, II, III, IV, V, VI, VII, and VIII, with over 90% being caused by five serotypes: Ia, Ib, II, III & V. The invention preferably uses a saccharide from one of these five serotypes. As shown in FIG. 2, the capsular saccharides of each of these five serotypes include: (a) a terminal N-acetyl-neuraminic acid (NeuNAc) residue (commonly referred to as sialic acid), which in all cases is linked 2→3 to a galactose residue; and (b) a N-acetyl-glucosamine residue (GlcNAc) within the trisaccharide core.

The carrier protein may be conjugated to a mixture of saccharide antigens as described in reference 34. The carrier protein may be conjugated to a single species of saccharide or may be conjugated to a number of different species of saccharides. In this invention, preferably the carrier proteins are conjugated to 2, 3, 4 or more different saccharide antigens. The antigens may be from the same or from antigenically distinct pathogens.

Thus, the carrier protein may be monovalent in that each carrier protein molecule is conjugated to saccharides from a single bacterial serogroup, or may be multivalent in that two or more (e.g. 2, 3, 4, 5, 6 or more) antigenically distinct saccharide antigens are conjugated to the same carrier protein molecule (for example, see reference 34).

Preferably, compositions of the invention comprise saccharide antigens from more than one serogroup of *N. meningitidis*, e.g. compositions may comprise saccharides conjugates from serogroups A+C, A+W135, A+Y, C+W135, C+Y, W135+Y, A+C+W135, A+C+Y, C+W135+Y, A+C+W135+Y, etc. Preferred compositions comprise saccharides from serogroups C and Y. Other preferred compositions comprise saccharides from serogroups C, W135 and Y. Particularly preferred compositions comprise saccharides from serogroups A, C, W135 and Y.

In other combinations, the carrier protein may be conjugated to a Hib saccharide conjugate and a saccharide from at least one serogroup of *N. meningitidis*, preferably from more than one serogroup of *N. meningitidis*. For example, a carrier protein may be conjugated to a Hib saccharide and saccharides from one or more (i.e. 1, 2, 3 or 4) of *N. meningitidis* serogroups A, C, W135 and Y. Other combinations of saccharides from the pathogens mentioned above are also provided.

Preparation of Capsular Saccharide Antigens

Methods for the preparation of capsular saccharide antigens are well known. For example, ref. 35 describes the preparation of saccharide antigens from *N. meningitidis*. The preparation of saccharide antigens from *H. influenzae* is described in chapter 14 of ref. 36. The preparation of saccharide antigens and conjugates from *S. pneumoniae* is described in the art. For example, Prevenar™ is a 7-valent pneumococcal conjugate vaccine. Processes for the preparation of saccharide antigens from *S. agalactiae* are described in detail in refs. 37, 38 and 39. Preferred processes for the preparation of saccharide antigens from *S. agalactiae* are described in reference 40. Capsular saccharides can be purified by known techniques, as described in several references herein.

The saccharide antigens may be chemically modified. For instance, they may be modified to replace one or more hydroxyl groups with blocking groups. This is particularly useful for meningococcal serogroup A where the acetyl groups may be replaced with blocking groups to prevent hydrolysis [41]. Such modified saccharides are still serogroup A saccharides within the meaning of the present invention.

In particular, the saccharide antigen from GBS may be modified. For example, when the saccharide antigen is the *Streptococcus agalactiae* serotype V capsular saccharide, then the saccharide antigen may be modified as described in ref. 42. In particular, the *Streptococcus agalactiae* serotype V capsular saccharide may be desialylated (FIG. 3). Desialylated GBS serotype V capsular saccharide may be prepared by treating purified GBS serotype V capsular saccharide under mildly acidic conditions (e.g. 0.1M sulphuric acid at 80° C. for 60 minutes) or by treatment with neuraminidase, as described in reference 42. A preferred method for preparing desialylated GBS serotype V capsular saccharide is by treating the purified saccharide with 1M acetic acid at 81° C.+/−3 C.° for 2 h.

The saccharide may be chemically modified relative to the capsular saccharide as found in nature. For example, the saccharide may be de-O-acetylated (partially or fully), de-N-acetylated (partially or fully), N-propionylated (partially or fully), etc. De-acetylation may occur before, during or after conjugation, but preferably occurs before conjugation. Depending on the particular saccharide, de-acetylation may or may not affect immunogenicity e.g. the NeisVac-C™ vaccine uses a de-O-acetylated saccharide, whereas Menjugate™ is acetylated, but both vaccines are effective. The effect of de-acetylation etc. can be assessed by routine assays.

Capsular saccharides may be used in the form of oligosaccharides. These are conveniently formed by fragmentation of purified capsular polysaccharide (e.g. by hydrolysis), which will usually be followed by purification of the fragments of the desired size. Fragmentation of polysaccharides is preferably performed to give a final average degree of polymerisation (DP) in the oligosaccharide of less than 30. DP can conveniently be measured by ion exchange chromatography or by colorimetric assays [43].

If hydrolysis is performed, the hydrolysate will generally be sized in order to remove short-length oligosaccharides [44]. This can be achieved in various ways, such as ultrafiltration followed by ion-exchange chromatography. Oligosaccharides with a degree of polymerisation of less than or equal to about 6 are preferably removed for serogroup A meningococcus, and those less than around 4 are preferably removed for serogroups W135 and Y.

Carrier-Saccharide Conjugates

Conjugates purified by the method of the invention may include small amounts of free (i.e. unconjugated) carrier. When a given carrier protein is present in both free and conjugated form in a composition following purification by the method of the invention, the unconjugated form is preferably no more than 5% of the total amount of the carrier protein in the composition as a whole (by weight), and more preferably present at less than 2%, more preferably less than 1%, preferably less than 0.5%.

Conjugates with a saccharide:protein ratio (w/w) of between 1:5 (i.e. excess protein) and 5:1 (i.e. excess saccharide) may be purified by the method of the invention e.g. ratios between 1:2 and 5:1 and ratios between 1:1.25 and 1:2.5. As described in reference 45, different meningococcal serogroup conjugates in a mixture can have different saccharide:protein ratios e.g. one may have a ratio of between 1:2 & 1:5, whereas another has a ratio between 5:1 & 1:1.99.

Any suitable conjugation reaction can be used, with any suitable linker where necessary. Attachment of the saccharide antigen to the carrier is preferably via a —NH$_2$ group e.g. in the side chain of a lysine residue in a carrier protein, or of an arginine residue. Where a saccharide has a free aldehyde group then this can react with an amine in the carrier to form a conjugate by reductive amination. Attachment may also be via a —SH group e.g. in the side chain of a cysteine residue.

The saccharide will typically be activated or functionalised prior to conjugation. Activation may involve, for example, cyanylating reagents such as CDAP (e.g. 1-cyano-4-dimethylamino pyridinium tetrafluoroborate [46, 47, etc.]). Other suitable techniques use carbodiimides, hydrazides, active esters, norborane, p-nitrobenzoic acid, N-hydroxysuccinimide, S-NHS, EDC, TSTU (see also the introduction to reference 48).

When the saccharide antigen is a *Streptococcus agalactiae* capsular saccharide, conjugation typically involves reductive amination of the saccharide to a carrier protein, as described in reference 37. The reductive amination involves an amine group on the side chain of an amino acid in the carrier and an aldehyde group in the saccharide. As GBS capsular saccharides do not include an aldehyde group in their natural form then this is generated before conjugation by periodate oxidation of a portion of the saccharide's sialic acid residues, as shown in FIG. 4 [37,49]. Conjugation of a *Streptococcus agalactiae* capsular saccharide to a carrier protein may also be carried using the methods described in reference 50.

As described in reference 51, a mixture of conjugates can include one conjugate with direct saccharide/protein linkage and another conjugate with linkage via a linker. This arrangement applies particularly when using saccharide conjugates from different meningococcal serogroups e.g. MenA and MenC saccharides may be conjugated via a linker, whereas MenW135 and MenY saccharides may be conjugated directly to a carrier protein. Such conjugates may be purified by the method of the invention.

The concentration of carrier (conjugated and unconjugated) from each conjugate may be no more than 100 μg/ml e.g. <30 μg/ml of carrier protein from each conjugate. Some compositions include a total concentration of carrier of less than 500 μg/ml e.g. <400 μg/ml, <300 μg/ml, <200 μg/ml, <100 μg/ml, <50 μg/ml, etc.

Linkers

Linkages via a linker group may be made using any known procedure, for example, the procedures described in references 52 and 53. One type of linkage involves reductive amination of the saccharide, coupling the resulting amino group with one end of an adipic acid linker group, and then coupling the carrier protein to the other end of the adipic acid linker group [54, 55]. Other linkers include B-propionamido [56], nitrophenyl-ethylamine [57], haloacyl halides [58], glycosidic linkages [59], 6-aminocaproic acid [60], ADH [61], C4 to C12 moieties [62] etc. As an alternative to using a linker, direct linkage can be used. Direct linkages to the protein may comprise oxidation of the polysaccharide followed by reductive amination with the protein, as described in, for example, references 63 and 64.

A process involving the introduction of amino groups into the saccharide (e.g. by replacing terminal =0 groups with —NH$_2$) followed by derivatisation with an adipic diester (e.g. adipic acid N-hydroxysuccinimido diester) and reaction with carrier protein is preferred.

A bifunctional linker may be used to provide a first group for coupling to an amine group in the saccharide and a second group for coupling to the carrier (typically for coupling to an amine in the carrier). The first group in the bifunctional linker is thus able to react with an amine group (—NH$_2$) on the saccharide. This reaction will typically involve an electrophilic substitution of the amine's hydrogen. The second group in the bifunctional linker is able to react with an amine group on the carrier. This reaction will again typically involve an electrophilic substitution of the amine.

Where the reactions with both the saccharide and the carrier involve amines then it is preferred to use a bifunctional linker of the formula X-L-X, where: the two X groups are the same as each other and can react with the amines; and where L is a linking moiety in the linker. A preferred X group is N-oxysuccinimide. L preferably has formula L'-L$^2$-L', where L' is carbonyl. Preferred L$^2$ groups are straight chain alkyls with 1 to 10 carbon atoms (e.g. $C_1, C_2, C_3, C_4, C_5, C_6, C_7, C_8, C_9, C_{10}$) e.g. —$(CH_2)_4$—.

Other X groups are those which form esters when combined with HO-L-OH, such as norborane, p-nitrobenzoic acid, and sulfo-N-hydroxysuccinimide.

Further bifunctional linkers for use with the invention include acryloyl halides (e.g. chloride) and haloacylhalides.

The linker will generally be added in molar excess to modified saccharide.

After conjugation, free and conjugated saccharides can be separated. There are many suitable methods, including hydrophobic chromatography, tangential ultrafiltration, diafiltration etc. [see also refs. 65 & 66, etc.].

Where the composition of the invention includes a depolymerised saccharide, it is preferred that depolymerisation precedes conjugation.

Hydroxyapatite

The hydroxyapatite (($Ca_5(PO_4)_3OH)_2$) used in the invention may be in one of number of forms known in the art. The hydroxyapatite may be in the form of crystals, a gel or a resin. The normal crystalline form may alternatively be sintered at high temperatures to modify it to a ceramic form (Bio-Rad).

Preferably the hydroxyapatite is in the form of a gel. Preferably, the gel is packed into a column, as commonly used in chromatography purification.

If the hydroxyapatite is in particulate form, preferably the particles have a diameter of 20 μm or more, preferably 40 μm or more, preferably 80 μm or more.

Preferably the hydroxyapatite has a dynamic binding capacity of >10 mg lysozyme per gram (e.g. 12.5, 15, 17.5, 20, 22.5, 25, 27.5, 30, 35, 40, 45, 50 or more).

pH

Preferably the method is carried out at a pH of between 6 and 8, more preferably 6.5 to 7.5, more preferably 7.2. pH7.2 is preferred as this helps to ensure the stability of the saccharide. The pH may be adjusted using acids/bases known in the art.

Phosphate Concentration

Different phosphate concentrations used in the method can have an effect on the yield of conjugate from the reaction. Preferably the phosphate concentration of the starting material and equilibration/post loading wash is 50 mM or less (i.e. 45, 40, 35, 30, 25, 20, 15, 10, 5 or less). Typically, a concentration of 35 mM is used. Higher concentrations may result in the inhibition of binding by the hydroxyapatite.

Typically a sodium phosphate buffer is used.

Further Antigens

As noted above, conjugates purified by the invention may be formulated as a pharmaceutical composition by the addition of a pharmaceutically acceptable diluent or carrier. Such compositions may also comprise one or more (e.g. 2, 3, 4, 5, 6, 7, 8, 9, 10 or more) further antigens, such as:

A. Bacterial Antigens

*Neisseria meningitidis*: meningococcal antigens may include proteins (such as those identified in references 67-73), saccharides (including a polysaccharide, oligosaccharide or lipopolysaccharide), or outer-membrane vesicles [74-77] purified or derived from a *N. meningitidis* serogroup such as A, C, W135, Y, and/or B. Meningococcal protein antigens may be selected from adhesins, autotransporters, toxins, iron acquisition proteins, and membrane associated proteins (preferably integral outer membrane proteins). See also refs. 78-86.

*Streptococcus pneumoniae*: *S. pneumoniae* antigens may include a saccharide (including a polysaccharide or an oligosaccharide) and/or protein from *S. pneumoniae*. Protein antigens may be selected, for example, from a protein identified in any of refs. 87-92. *S. pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, Sp101, Sp130, Sp125 or Sp133. See also refs. 93-99.

*Streptococcus pyogenes* (Group A *Streptococcus*): Group A *Streptococcus* antigens may include a protein identified in reference 100 or 101 (including GAS40), fusions of fragments of GAS M proteins (including those described in refs. 102-104), fibronectin binding protein (Sfb1), Streptococcal heme-associated protein (Shp), and Streptolysin S (SagA). See also refs. 100, 105 and 106.

*Moraxella catarrhalis*: *Moraxella* antigens include antigens identified in refs. 107 & 108, outer membrane protein antigens (HMW-OMP), C-antigen, and/or LPS. See also ref. 109.

*Bordetella pertussis*: Pertussis antigens include *petussis* holotoxin (PT) and filamentous haemagglutinin (FHA) from *B. pertussis*, optionally also in combination with pertactin and/or agglutinogens 2 and 3 antigen. See also refs. 110 & 111.

*Staphylococcus aureus*: *S. aureus* antigens include *S. aureus* type 5 and 8 capsular polysaccharides optionally conjugated to nontoxic recombinant *Pseudomonas aeruginosa* exotoxin A, such as StaphVAX™, or antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin). See also ref. 112.

*Clostridium tetani* (Tetanus): Tetanus antigens include tetanus toxoid (TT), preferably used as a carrier protein in conjunction/conjugated with the compositions of the present invention.

*Corynebacterium diphtheriae* (Diphtheria): Diphtheria antigens include diphtheria toxin or detoxified mutants thereof, such as CRM197. Additionally antigens capable of modulating, inhibiting or associated with ADP ribosylation are contemplated for combination/co-administration/conjugation with the compositions of the present invention. These diphtheria antigens may be used as carrier proteins.

*Haemophilus influenzae*: *H. influenzae* antigens include a saccharide antigen from type B, or protein D [24].

*Streptococcus agalactiae* (Group B *Streptococcus*): Group B *Streptococcus* antigens include protein antigens identified in refs. 100 and 113-116. For example, the antigens include proteins GBS80, GBS104, GBS276 and GBS322.

*Neisseria gonorrhoeae*: Gonococcal antigens include Por (or porin) protein, such as PorB [117], a transferring binding protein, such as TbpA and TbpB [118], an opacity protein (such as Opa), a reduction-modifiable protein (Rmp), and outer membrane vesicle (OMV) preparations [119]. See also refs. 67-69 & 120.

*Chlamydia trachomatis*: *C. trachomatis* antigens include antigens derived from serotypes A, B, Ba and C (agents of trachoma, a cause of blindness), serotypes $L_1$, $L_2$ & $L_3$ (associated with Lymphogranuloma venereum), and serotypes, D-K. *C. trachomatis* antigens may also include an antigen identified in refs. 116 & 121-123, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761). See also ref. 124.

*Salmonella typhi* (typhoid fever): Antigens include capsular polysaccharides preferably conjugates (Vi, e.g. vax-TyVi).

B. Viral Antigens

Orthomyxovirus: Viral antigens may be derived from an Orthomyxovirus, such as Influenza A, B and C. Orthomyxovirus antigens may be selected from one or more of the viral proteins, including hemagglutinin (HA), neuraminidase (NA), nucleoprotein (NP), matrix protein (M1), membrane protein (M2), one or more of the transcriptase components (PB1, PB2 and PA). Preferred antigens include HA and NA.

Influenza antigens may be derived from interpandemic (annual) flu strains. Alternatively influenza antigens may be derived from strains with the potential to cause a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens may be derived from Paramyxoviridae viruses, such as Pneumoviruses (RSV), Paramyxoviruses (PIV) and Morbilliviruses (Measles). [125-127].

Pneumovirus: Viral antigens may be derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. Pneumovirus antigens may be selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. Preferred Pneumovirus antigens include F, G and M. See, for example, ref. 128. Pneumovirus antigens may also be formulated in or derived from chimeric viruses. For example, chimeric RSV/PIV viruses may comprise components of both RSV and NV.

Paramyxovirus: Viral antigens may be derived from a Paramyxovirus, such as Parainfluenza virus types 1-4 (PIV), Mumps, Sendai viruses, Simian virus 5, Bovine parainfluenza virus and Newcastle disease virus. Preferably, the Paramyxovirus is PIV or Mumps. Paramyxovirus antigens may be selected from one or more of the following proteins: Hemagglutinin-Neuraminidase (HN), Fusion proteins F1 and F2, Nucleoprotein (NP), Phosphoprotein (P), Large protein (L), and Matrix protein (M). Preferred Paramyxovirus proteins include HN, F1 and F2. Paramyxovirus antigens may also be formulated in or derived from chimeric viruses. For example, chimeric RSV/PIV viruses may comprise components of both RSV and PIV. Commercially available mumps vaccines include live attenuated mumps virus, in either a monovalent form or in combination with measles and rubella vaccines (MMR).

Morbillivirus: Viral antigens may be derived from a Morbillivirus, such as Measles. Morbillivirus antigens may be selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Enterovirus: Viral antigens may be derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. Preferably, the Enterovirus is poliovirus. Enterovirus antigens are preferably selected from one or more of the following Capsid proteins VP1, VP2, VP3 and VP4. Commercially available polio vaccines include Inactivated Polio Vaccine (IPV) and oral poliovirus vaccine (OPV).

Heparnavirus: Viral antigens may be derived from an Heparnavirus, such as Hepatitis A virus (HAV). Commercially available HAV vaccines include inactivated HAV vaccine. [129,130].

Togavirus: Viral antigens may be derived from a Togavirus, such as a Rubivirus, an Alphavirus, or an Arterivirus. Antigens derived from Rubivirus, such as Rubella virus, are preferred. Togavirus antigens may be selected from E1, E2, E3, C, NSP-1, NSPO-2, NSP-3 or NSP-4. Togavirus antigens are preferably selected from E1, E2 or E3. Commercially available Rubella vaccines include a live cold-adapted virus, typically in combination with mumps and measles vaccines (MMR).

Hepadnavirus: Viral antigens may be derived from a Hepadnavirus, such as Hepatitis B virus. Hepadnavirus antigens may be selected from surface antigens (L, M and S), core antigens (HBc, HBe). Commercially available HBV vaccines include subunit vaccines comprising the surface antigen S protein [130,131].

Papovaviruses: Antigens may be derived from Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65. Preferably, HPV antigens are derived from serotypes 6, 11, 16 or 18. HPV antigens may be selected from capsid proteins (L1) and (L2), or E1-E7, or fusions thereof. HPV antigens are preferably formulated into virus-like particles (VLPs). Polyomyavirus viruses include BK virus and JK virus. Polyomavirus antigens may be selected from VP1, VP2 or VP3.

C. Antigen Formulations

In other aspects of the invention, methods of producing microparticles having adsorbed antigens are provided. The methods comprise: (a) providing an emulsion by dispersing a mixture comprising (i) water, (ii) a detergent, (iii) an organic solvent, and (iv) a biodegradable polymer selected from the group consisting of a poly($\alpha$-hydroxy acid), a polyhydroxy butyric acid, a polycaprolactone, a polyorthoester, a polyanhydride, and a polycyanoacrylate. The polymer is typically present in the mixture at a concentration of about 1% to about 30% relative to the organic solvent, while the detergent is typically present in the mixture at a weight-to-weight detergent-to-polymer ratio of from about 0.00001:1 to about 0.1:1 (more typically about 0.0001:1 to about 0.1:1, about 0.001:1 to about 0.1:1, or about 0.005:1 to about 0.1:1); (b) removing the organic solvent from the emulsion; and (c) adsorbing an antigen on the surface of the microparticles. In certain embodiments, the biodegradable polymer is present at a concentration of about 3% to about 10% relative to the organic solvent.

Microparticles for use herein will be formed from materials that are sterilizable, non-toxic and biodegradable. Such materials include, without limitation, poly($\alpha$-hydroxy acid), polyhydroxybutyric acid, polycaprolactone, polyorthoester, polyanhydride, PACA, and polycyanoacrylate. Preferably, microparticles for use with the present invention are derived from a poly($\alpha$-hydroxy acid), in particular, from a poly (lactide) ("PLA") or a copolymer of D,L-lactide and glycolide or glycolic acid, such as a poly(D,L-lactide-co-glycolide) ("PLG" or "PLGA"), or a copolymer of D,L- lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered macromolecule. These parameters are discussed more fully below.

Medical Methods and Uses

Once formulated, the compositions of the invention can be administered directly to a subject. The subjects to be treated can be animals; in particular, human subjects can be treated. The compositions may be formulated as vaccines that are particularly useful for vaccinating children and teenagers. They may be delivered by systemic and/or mucosal routes.

Typically, the compositions are prepared as injectables, either as liquid solutions or suspensions; solid forms suitable for solution in, or suspension in, liquid vehicles prior to injection may also be prepared. Direct delivery of the compositions will generally be parenteral (e.g. by injection, either subcutaneously, intraperitoneally, intravenously or intramuscularly or delivered to the interstitial space of a tissue). The compositions can also be administered into a lesion. Other modes of administration include oral and pulmonary administration, suppositories, and transdermal or transcutaneous applications (e.g. see ref. 132), needles, and hyposprays. Dosage treatment may be a single dose schedule or a multiple dose schedule (e.g. including booster doses).

Vaccines of the invention are preferably sterile. They are preferably pyrogen-free. They are preferably buffered e.g. at between pH 6 and pH 8, generally around pH 7. Where a vaccine comprises an aluminium hydroxide salt, it is preferred to use a histidine buffer [133].

Vaccines of the invention may comprise detergent (e.g. a TWEEN™, such as TWEEN 80™) at low levels (e.g. <0.01%). Vaccines of the invention may comprise a sugar alcohol (e.g. mannitol) or trehalose e.g. at around 15 mg/ml, particularly if they are to be or have been lyophilised.

Optimum doses of individual antigens can be assessed empirically. In general, however, conjugate antigens purified by the method of the invention will be administered at a dose of between 0.1 and 100 μg of each saccharide per dose, with a typical dosage volume of 0.5 ml. The dose is typically between 5 and 20 μg per saccharide per dose. These values are measured as saccharide in the conjugate.

Vaccines according to the invention may either be prophylactic (i.e. to prevent infection) or therapeutic (i.e. to treat disease after infection), but will typically be prophylactic.

The invention provides a conjugate purified by the method of the invention for use in medicine.

The invention also provides a method of raising an immune response in a patient, comprising administering to a patient a conjugate according to the invention. The immune response is preferably protective against meningococcal disease, pneumococcal disease or *H. influenzae* type B and may comprise a humoral immune response and/or a cellular immune response. The patient is preferably a child. The method may raise a booster response, in a patient that has already been primed against meningococcus, pneumococcus or *H. influenzae* type B. In other embodiments, the immune response is protective against *Streptococcus agalactiae* and may comprise a humoral immune response and/or a cellular immune response. The patient is preferably a child, neonate or pregnant adult. The method may raise a booster response, in a patient that has already been primed against *Streptococcus agalactiae*.

The invention also provides the use of a conjugate of the invention in the manufacture of a medicament for raising an immune response in a patient, wherein said patient has been pre-treated with a different saccharide antigen to that comprised within the composition conjugated to a carrier.

The invention also provides the use of a conjugate in the manufacture of a medicament for raising an immune response in a patient, wherein said patient has been pre-treated with the same saccharide antigen as that comprised within the composition conjugated to a different carrier.

The medicament is preferably an immunogenic composition (e.g. a vaccine). The medicament is preferably for the prevention and/or treatment of a disease caused by a *Neisseria* (e.g. meningitis, septicaemia, gonorrhoea etc.), by *H. influenzae* (e.g. otitis media, bronchitis, pneumonia, cellulitis, pericarditis, meningitis etc.) or by pneumococcus (e.g. meningitis, sepsis, pneumonia, etc). The prevention and/or treatment of bacterial meningitis is thus preferred. In other embodiments, the medicament is for the prevention and/or treatment of a disease caused by *Streptococcus agalactiae*. The prevention and/or treatment of such diseases is thus also preferred.

Vaccines can be tested in standard animal models (e.g. see ref. 134).

Adjuvants

Conjugates of the invention may be administered in conjunction with other immunoregulatory agents. In particular, compositions will usually include an adjuvant. Adjuvants which may be used in compositions of the invention include, but are not limited to:

A. Mineral-Containing Compositions

Mineral containing compositions suitable for use as adjuvants in the invention include mineral salts, such as aluminium salts and calcium salts. Such mineral compositions may include mineral salts such as hydroxides (e.g. oxyhydroxides), phosphates (e.g. hydroxyphosphates, orthophosphates), sulphates, etc. [e.g. see chapters 8 & 9 of ref. 135], or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt [136].

Aluminum salts may be included in compositions of the invention such that the dose of $Al^{3+}$ is between 0.2 and 1.0 mg per dose.

A typical aluminium phosphate adjuvant is amorphous aluminium hydroxyphosphate with $PO_4$/Al molar ratio between 0.84 and 0.92, included at 0.6 mg $Al^{3+}$/ml. Adsorption with a low dose of aluminium phosphate may be used e.g. between 50 and 100 μg $Al^{3+}$ per conjugate per dose. Where an aluminium phosphate it used and it is desired not to adsorb an antigen to the adjuvant, this is favoured by including free phosphate ions in solution (e.g. by the use of a phosphate buffer).

B. Oil Emulsions

Oil emulsion compositions suitable for use as adjuvants with conjugates of the invention include squalene-water emulsions, such as MF59 (5% squalene, 0.5% TWEEN 80™, and 0.5% SPAN 85™, formulated into submicron particles using a microfluidizer) [Chapter 10 of ref. 135; see also refs. 137-139]. MF59 is used as the adjuvant in the FLUAD™ influenza virus trivalent subunit vaccine. The MF59 emulsion advantageously includes citrate ions e.g. 10 mM sodium citrate buffer.

Particularly preferred adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v TWEEN 80™ (polyoxyelthylenesorbitan monooleate), and/or 0.25-1.0% SPAN 85™ (sorbitan trioleate), and, optionally, N-acetyl-muramyl-L-alanyl-D-isogluatminyl-L-alanine-2-(1'-2'-di-palmitoyl-sn-glycero-3-hydroxyphosphophoryloxy)-ethyl-amine (MTP-PE). Submicron oil-in-water emulsions, methods of making the same and immunostimulating agents, such as muramyl peptides, for use in the compositions, are described in detail in references 137 & 140-141.

An emulsion of squalene, a tocopherol, and TWEEN 80™ can be used. The emulsion may include phosphate buffered saline. It may also include SPAN 85™ (e.g. at 1%) and/or lecithin. These emulsions may have from 2 to 10% squalene, from 2 to 10% tocopherol and from 0.3 to 3% TWEEN 80™, and the weight ratio of squalene:tocopherol is preferably <1 as this provides a more stable emulsion. One such emulsion can be made by dissolving TWEEN 80™ in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

An emulsion of squalene, a tocopherol, and a TRITON™ detergent (e.g. Triton TRITON X-100™ can be used.

An emulsion of squalane, polysorbate 80 and poloxamer 401 ("PLURONIC™ L121") can be used. The emulsion can be formulated in phosphate buffered saline, pH 7.4. This emulsion is a useful delivery vehicle for muramyl dipeptides, and has been used with threonyl-MDP in the "SAF-1" adjuvant [142] (0.05-1% Thr-MDP, 5% squalane, 2.5% PLURONIC™ L121 and 0.2% polysorbate 80). It can also be used without the Thr-MDP, as in the "AF" adjuvant [143] (5% squalane, 1.25% PLURONIC™ L121 and 0.2% polysorbate 80). Microfluidisation is preferred.

Complete Freund's adjuvant (CFA) and incomplete Freund's adjuvant (IFA) may also be used as adjuvants.

C. Saponin Formulations [Chapter 22 of Ref 135]

Saponin formulations may also be used as adjuvants of conjugates of the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponin can also be commercially obtained from *Smilax ornata* (sarsaparilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 144. Saponin formulations may also comprise a sterol, such as cholesterol [145].

Combinations of saponins and cholesterols can be used to form unique particles called immunostimulating complexs (ISCOMs) [chapter 23 of ref. 135]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 145-147. Optionally, the ISCOMS may be devoid of additional detergent(s) [148].

A review of the development of saponin based adjuvants can be found in refs. 149 & 150.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 151-156. Virosomes are discussed further in, for example, ref. 157

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 158. Such "small particles" of 3dMPL are small enough to be sterile filtered through a 0.22 μm membrane [158]. Other non-toxic LPS derivatives include monophosphoryl lipid A mimics, such as aminoalkyl glucosaminide phosphate derivatives e.g. RC-529 [159,160].

Lipid A derivatives include derivatives of lipid A from *Escherichia coli* such as OM-174. OM-174 is described for example in refs. 161 & 162.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 163, 164 and 165 disclose possible analog substitutions e.g. replacement of guanosine with 2'-deoxy-7-deazaguanosine. The adjuvant effect of CpG oligonucleotides is further discussed in refs. 166-171.

The CpG sequence may be directed to TLR9, such as the motif GTCGTT or TTCGTT [172]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 173-175. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 172 & 176-178.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 179 and as parenteral adjuvants in ref. 180. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 181-188. Numerical reference for amino acid substitutions is preferably based on the alignments of the A and B subunits of ADP-ribosylating toxins set forth in ref. 189, specifically incorporated herein by reference in its entirety.

Compounds of formula I, II or III, or salts thereof, can also be used as adjuvants:

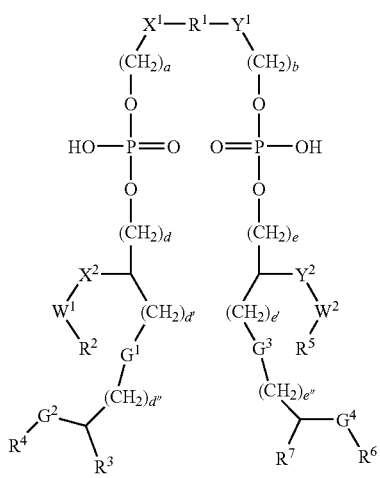

I

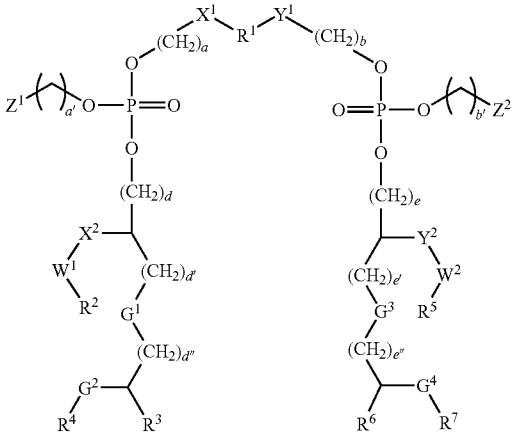

II

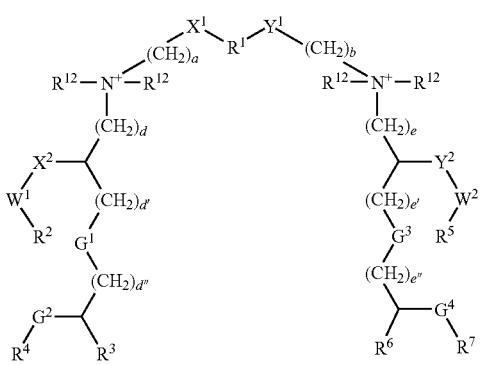

III as defined in reference 190, such as 'ER 803058', 'ER 803732', 'ER 804053', ER 804058', 'ER 804059', 'ER 804442', 'ER 804680', 'ER 804764', ER 803022 or 'ER 804057' e.g.:

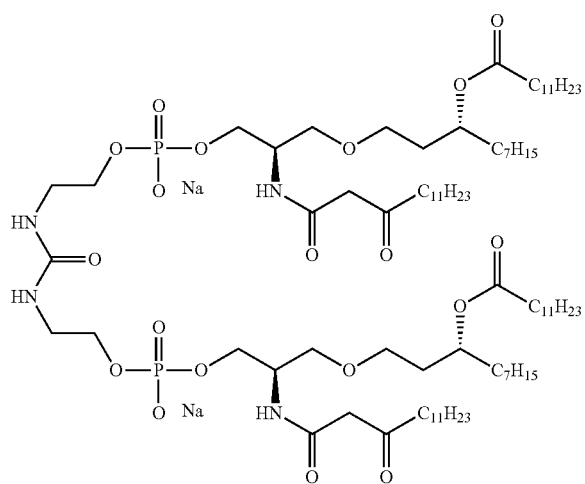

ER804057

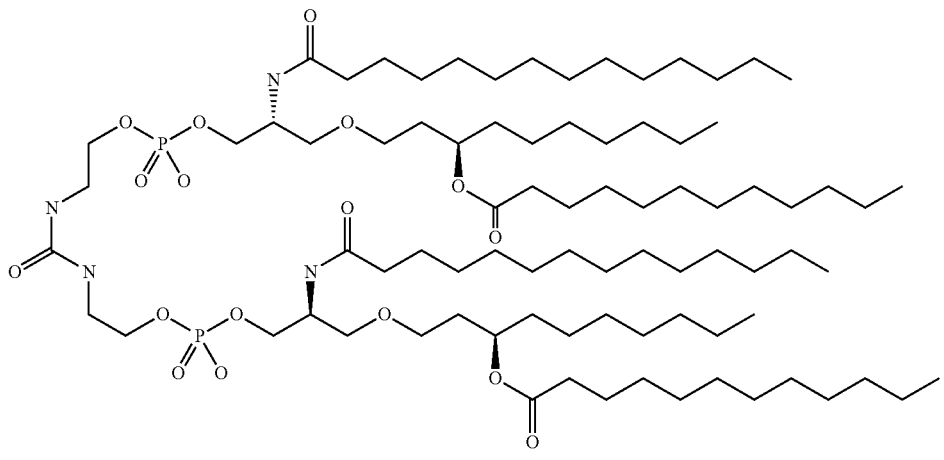

F. Human Immunomodulators

Human immunomodulators suitable for use as adjuvants in the invention include cytokines, such as interleukins (e.g. IL-1, IL-2, IL-4, IL-5, IL-6, IL-7, IL-12 [191], IL-23, IL-27 [192] etc.) [193], interferons (e.g. interferon-γ), macrophage colony stimulating factor, tumor necrosis factor and macrophage inflammatory protein-1alpha (MIP-1alpha) and MIP-1beta [194].

G. Bioadhesives and Mucoadhesives

Bioadhesives and mucoadhesives may also be used as adjuvants in the invention. Suitable bioadhesives include esterified hyaluronic acid microspheres [195] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [196].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of ref. 135)

Examples of liposome formulations suitable for use as adjuvants are described in refs. 197-199.

J. Polyoxyethylene Ether and Polyoxyethylene Ester Formulations

Adjuvants suitable for use in the invention include polyoxyethylene ethers and polyoxyethylene esters [200]. Such formulations further include polyoxyethylene sorbitan ester surfactants in combination with an octoxynol [201] as well as polyoxyethylene alkyl ethers or ester surfactants in combination with at least one additional non-ionic surfactant such as an octoxynol [202]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP (poly[di(carboxylatophenoxy)phosphazene]) formulations are described, for example, in refs. 203 and 204.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use as adjuvants in the invention include Imiquamod and its homologues (e.g. "Resiquimod 3M"), described further in refs. 205 and 206.

N. Thiosemicarbazone Compounds.

Examples of thiosemicarbazone compounds, as well as methods of formulating, manufacturing, and screening for compounds all suitable for use as adjuvants in the invention include those described in ref. 207. The thiosemicarbazones are particularly effective in the stimulation of human peripheral blood mononuclear cells for the production of cytokines, such as TNF-α.

O. Tryptanthrin Compounds.

Examples of tryptanthrin compounds, as well as methods of formulating, manufacturing, and screening for compounds all suitable for use as adjuvants in the invention include those described in ref. 208. The tryptanthrin compounds are particularly effective in the stimulation of human peripheral blood mononuclear cells for the production of cytokines, such as TNF-α.

P. Nucleoside Analogs

Various nucleoside analogs can be used as adjuvants, such as (a) Isatorabine (ANA-245; 7-thia-8-oxoguanosine):

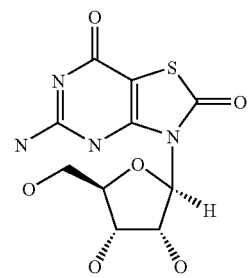 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 209 to 211; (f) a compound having the formula:

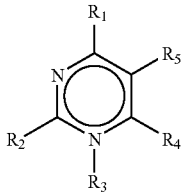

wherein:
- $R_1$ and $R_2$ are each independently H, halo, —$NR_aR_b$, —OH, $C_{1-6}$ alkoxy, substituted $C_{1-6}$ alkoxy, heterocyclyl, substituted heterocyclyl, $C_{6-10}$ aryl, substituted $C_{6-10}$ aryl, $C_{1-6}$ alkyl, or substituted $C_{1-6}$ alkyl;
- $R_3$ is absent, H, $C_{1-6}$ alkyl, substituted $C_{1-6}$ alkyl, $C_{6-10}$ aryl, substituted $C_{6-10}$ aryl, heterocyclyl, or substituted heterocyclyl;
- $R_4$ and $R_5$ are each independently H, halo, heterocyclyl, substituted heterocyclyl, —C(O)—$R_d$, $C_{1-6}$ alkyl, substituted $C_{1-6}$ alkyl, or bound together to form a 5 membered ring as in $R_{4-5}$:

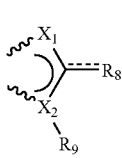

$R_{4-5}$ the binding being achieved at the bonds indicated by a ⁓

- $X_1$ and $X_2$ are each independently N, C, O, or S;
- $R_8$ is H, halo, —OH, $C_{1-6}$ alkyl, $C_{2-6}$ alkenyl, $C_{2-6}$ alkynyl, —OH, —$NR_aR_b$, —$(CH_2)_n$—O—$R_c$, —O—($C_{1-6}$ alkyl), —$S(O)_pR_e$, or —C(O)—$R_d$;
- $R_9$ is H, $C_{1-6}$ alkyl, substituted $C_{1-6}$ alkyl, heterocyclyl, substituted heterocyclyl or $R_{9a}$, wherein $R_{9a}$ is:

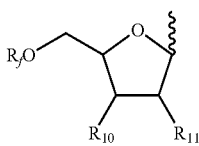

$R_{9a}$ the binding being achieved at the bond indicated by a ⁓

- $R_{10}$ and $R_{11}$ are each independently H, halo, $C_{1-6}$ alkoxy, substituted $C_{1-6}$ alkoxy, —$NR_aR_b$, or —OH;
- each $R_a$ and $R_b$ is independently H, $C_{1-6}$ alkyl, substituted $C_{1-6}$ alkyl, —$C(O)R_d$, $C_{6-10}$ aryl;
- each $R_c$ is independently H, phosphate, diphosphate, triphosphate, $C_{1-6}$ alkyl, or substituted $C_{1-6}$ alkyl;
- each $R_d$ is independently H, halo, $C_{1-6}$ alkyl, substituted $C_{1-6}$ alkyl, $C_{1-6}$ alkoxy, substituted $C_{1-6}$ alkoxy, —$NH_2$, —$NH(C_{1-6}$ alkyl), —NH(substituted $C_{1-6}$ alkyl), —$N(C_{1-6}$ alkyl)$_2$, —N(substituted $C_{1-6}$ alkyl)$_2$, $C_{6-10}$ aryl, or heterocyclyl;
- each $R_e$ is independently H, $C_{1-6}$ alkyl, substituted $C_{1-6}$ alkyl, $C_{6-10}$ aryl, substituted $C_{6-10}$ aryl, heterocyclyl, or substituted heterocyclyl;
- each $R_f$ is independently H, $C_{1-6}$ alkyl, substituted $C_{1-6}$ alkyl, —$C(O)R_d$, phosphate, diphosphate, or triphosphate;
- each n is independently 0, 1, 2, or 3;
- each p is independently 0, 1, or 2; or or (g) a pharmaceutically acceptable salt of any of (a) to (f), a tautomer of any of (a) to (f), or a pharmaceutically acceptable salt of the tautomer.

Q. Lipids Linked to a Phosphate-Containing Acyclic Backbone

Adjuvants containing lipids linked to a phosphate-containing acyclic backbone include the TLR4 antagonist E5564 [212,213]:

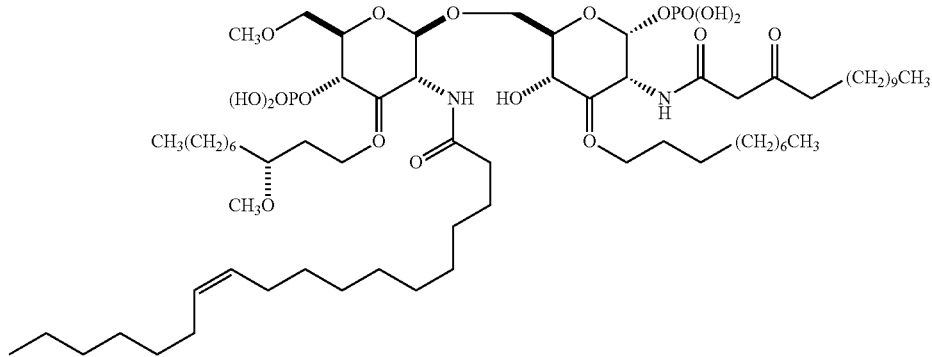

R. Small Molecule Immunopotentiators (SMIPs)
SMIPs include:
N2-methyl-1-(2-methylpropyl)-1H-imidazo[4,5-c]quinoline-2,4-diamine;
N2,N2-dimethyl-1-(2-methylpropyl)-1H-imidazo[4,5-c]quinoline-2,4-diamine;
N2-ethyl-N2-methyl-1-(2-methylpropyl)-1H-imidazo[4,5-c]quinoline-2,4-diamine;
N2-methyl-1-(2-methylpropyl)-N2-propyl-1H-imidazo[4,5-c]quinoline-2,4-diamine;
1-(2-methylpropyl)-N2-propyl-1H-imidazo[4,5-c]quinoline-2,4-diamine;
N2-butyl-1-(2-methylpropyl)-1H-imidazo[4,5-c]quinoline-2,4-diamine;

N2-butyl-N2-methyl-1-(2-methylpropyl)-1H-imidazo[4,5-c]quinoline-2,4-diamine;
N2-methyl-1-(2-methylpropyl)-N2-pentyl-1H-imidazo[4,5-c]quinoline-2,4-diamine;
N2-methyl-1-(2-methylpropyl)-N2-prop-2-enyl-1H-imidazo[4,5-c]quinoline-2,4-diamine;
1-(2-methylpropyl)-2-[(phenylmethyl)thio]-1H-imidazo[4,5-c]quinolin-4-amine;
1-(2-methylpropyl)-2-(propylthio)-1H-imidazo[4,5-c]quinolin-4-amine;
2-[[4-amino-1-(2-methylpropyl)-1H-imidazo[4,5-c]quinolin-2-yl](methyl)amino]ethanol;
2-[[4-amino-1-(2-methylpropyl)-1H-imidazo[4,5-c]quinolin-2-yl](methyl)amino]ethyl acetate;
4-amino-1-(2-methylpropyl)-1,3-dihydro-2H-imidazo[4,5-c]quinolin-2-one;
N2-butyl-1-(2-methylpropyl)-N4,N4-bis(phenylmethyl)-1H-imidazo[4,5-c]quinoline-2,4-diamine;
N2-butyl-N2-methyl-1-(2-methylpropyl)-N4,N4-bis(phenylmethyl)-1H-imidazo[4,5-c]quinoline-2,4-diamine;
N2-methyl-1-(2-methylpropyl)-N4,N4-bis(phenylmethyl)-1H-imidazo[4,5-c]quinoline-2,4-diamine;
N2,N2-dimethyl-1-(2-methylpropyl)-N4,N4-bis(phenylmethyl)-1H-imidazo[4,5-c]quinoline-2,4-diamine;
1-{4-amino-2-[methyl(propyl)amino]-1H-imidazo[4,5-c]quinolin-1-yl}-2-methylpropan-2-ol;
1-[4-amino-2-(propylamino)-1H-imidazo[4,5-c]quinolin-1-yl]-2-methylpropan-2-ol;
N4,N4-dibenzyl-1-(2-methoxy-2-methylpropyl)-N2-propyl-1H-imidazo[4,5-c]quinoline-2,4-diamine.

S. Proteosomes

One adjuvant is an outer membrane protein proteosome preparation prepared from a first Gram-negative bacterium in combination with a liposaccharide preparation derived from a second Gram-negative bacterium, wherein the outer membrane protein proteosome and liposaccharide preparations form a stable non-covalent adjuvant complex. Such complexes include "IVX-908", a complex comprised of Neisseria meningitidis outer membrane and lipopolysaccharides. They have been used as adjuvants for influenza vaccines [214].

T. Other Adjuvants

Other substances that act as immunostimulating agents are disclosed in references 135 and 215. Further useful adjuvant substances include:

Methyl inosine 5'-monophosphate ("MIMP") [216].
A polyhydroxlated pyrrolizidine compound [217], such as one having formula:

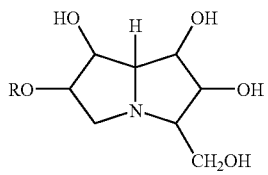

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A gamma inulin [218] or derivative thereof, such as algammulin.

Compounds disclosed in reference 219.

Compounds disclosed in reference 220, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [221,222], Hydrapthalamide compounds, Benzophenone compounds, Isoxazole compounds, Sterol compounds, Quinazilinone compounds, Pyrrole compounds [223], Anthraquinone compounds, Quinoxaline compounds, Triazine compounds, Pyrazalopyrimidine compounds, and Benzazole compounds [224].

Loxoribine (7-allyl-8-oxoguanosine) [225].

A formulation of a cationic lipid and a (usually neutral) co-lipid, such as aminopropyl-dimethyl-myristoleyloxy-propanaminium bromide-diphytanoylphosphatidyl-ethanolamine ("Vaxfectin™") or aminopropyl-dimethyl-bis-dodecyloxy-propanaminium bromide-dioleoylphosphatidyl-ethanolamine ("GAP-DLRIE:DOPE"). Formulations containing (±)-N-(3-aminopropyl)-N,N-dimethyl-2,3-bis (syn-9-tetradeceneyloxy)-1-propanaminium salts are preferred [226].

The invention may also comprise combinations of aspects of one or more of the adjuvants identified above. For example, the following combinations may be used as adjuvant compositions in the invention: (1) a saponin and an oil-in-water emulsion [227]; (2) a saponin (e.g. QS21)+a non-toxic LPS derivative (e.g. 3dMPL) [228]; (3) a saponin (e.g. QS21)+a nontoxic LPS derivative (e.g. 3dMPL)+a cholesterol; (4) a saponin (e.g. QS21)+3dMPL+IL-12 (optionally+a sterol) [229]; (5) combinations of 3dMPL with, for example, QS21 and/or oil-in-water emulsions [230]; (6) SAF, containing 10% squalane, 0.4% TWEEN 80™, 5% pluronic PLURONIC™-block polymer L121, and thr-MDP, either microfluidized into a submicron emulsion or vortexed to generate a larger particle size emulsion. (7) RIBI™ adjuvant system (RAS), (Ribi ImmunoChem) containing 2% squalene, 0.2% TWEEN 80™, and one or more bacterial cell wall components from the group consisting of monophosphorylipid A (MPL), trehalose dimycolate (TDM), and cell wall skeleton (CWS), preferably MPL+CWS (DETOX™); (8) one or more mineral salts (such as an aluminum salt)+a non-toxic derivative of LPS (such as 3dMPL); and (9) one or more mineral salts (such as an aluminum salt)+an immunostimulatory oligonucleotide (such as a nucleotide sequence including a CpG motif).

DEFINITIONS

The term "comprising" encompasses "including" as well as "consisting" e.g. a composition "comprising" X may consist exclusively of X or may include something additional e.g. X+Y.

The term "about" in relation to a numerical value x means, for example, x+10%. All numerical values herein can be considered to be qualified by "about", unless the context indicates otherwise.

The word "substantially" does not exclude "completely" e.g. a composition which is "substantially free" from Y may be completely free from Y. Where necessary, the word "substantially" may be omitted from the definition of the invention.

BRIEF DESCRIPTION OF DRAWINGS

FIG. 2 shows the repeating structures of capsular saccharides in GBS serotypes Ia, Ib, II, III & V.

MODES FOR CARRYING OUT THE INVENTION

Example 1

Conjugate Preparation

Figure 1:
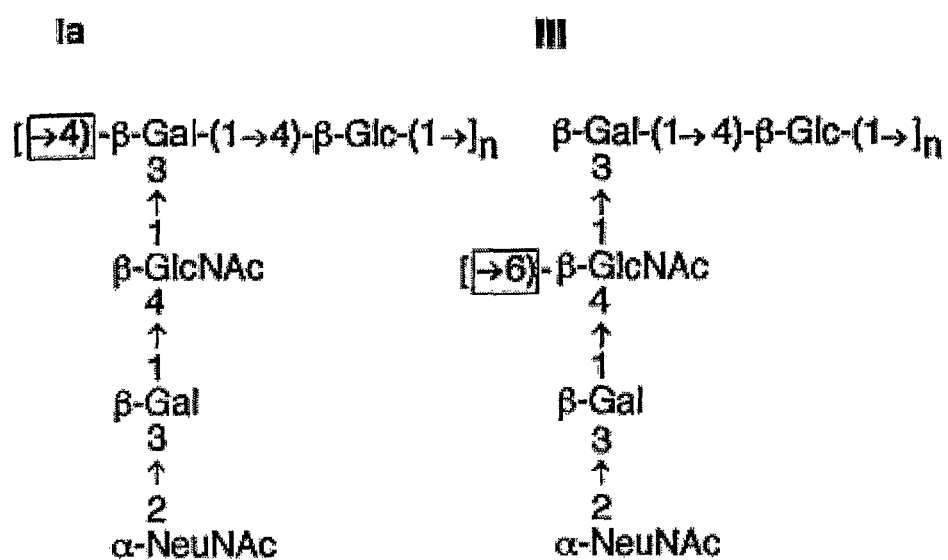
FIG. 1 shows the difference between the repeating structures in GBS serotypes Ia and III.
Figure 3:
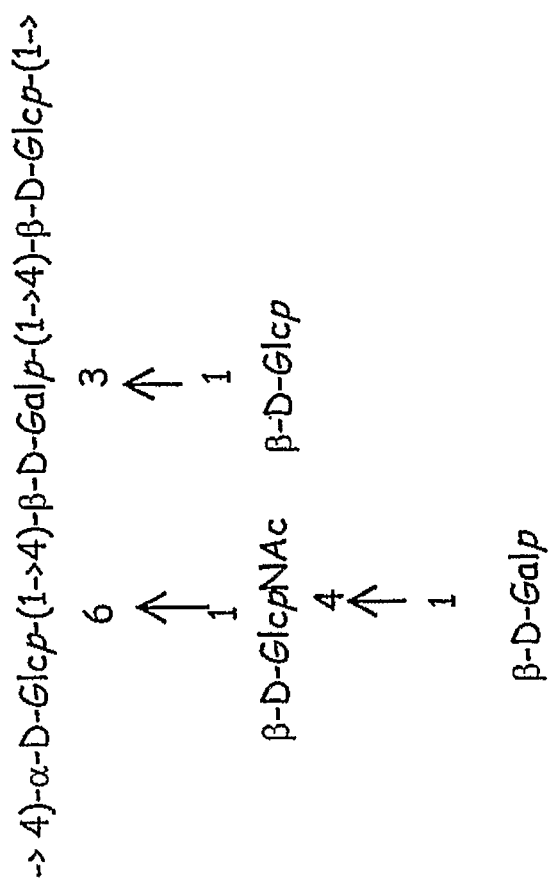
FIG. 3 shows the repeating structure of the desialylated form of the capsular polysaccharide from GBS serotype V.
Figure 4:
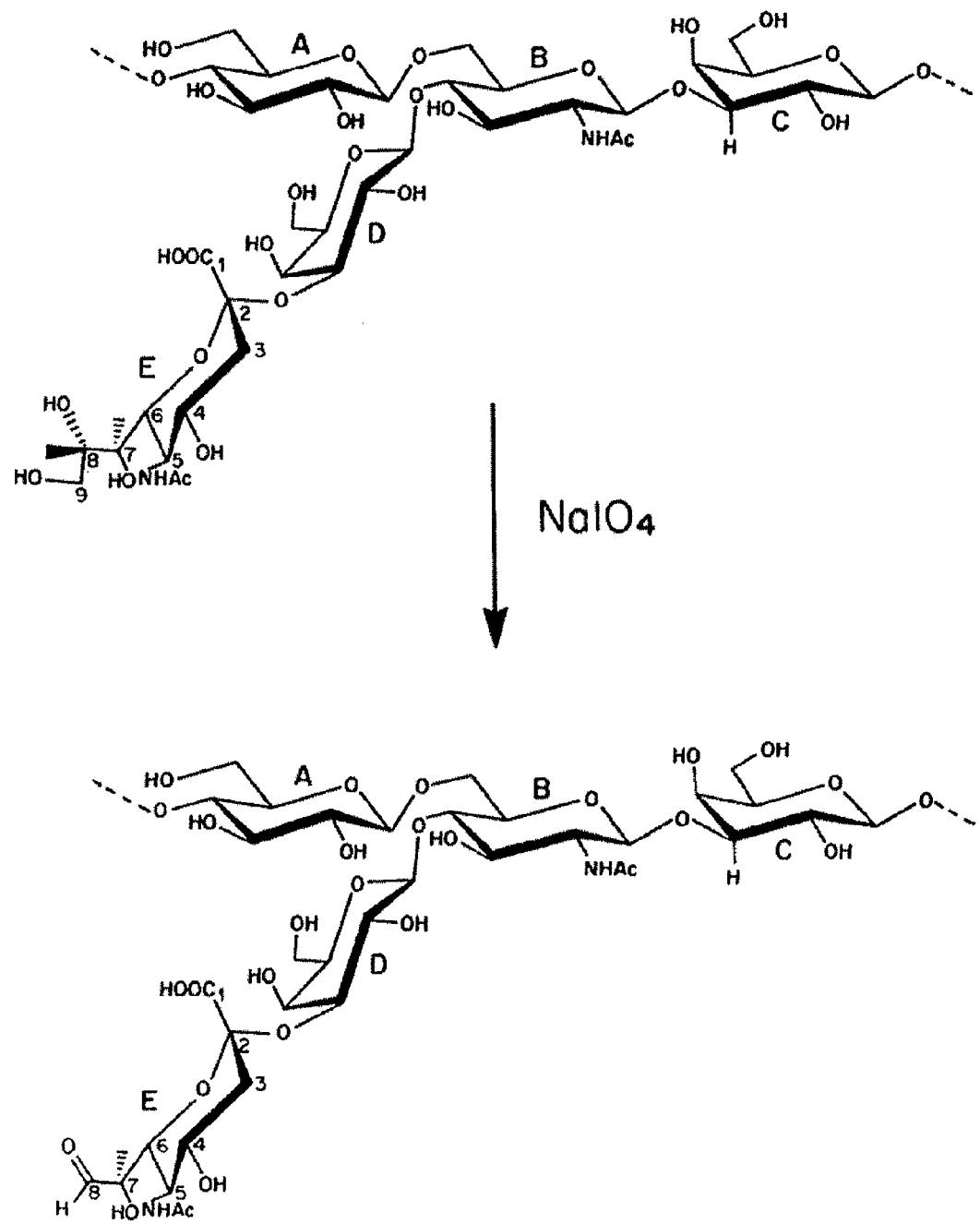
FIG. 4 shows periodate oxidation of a terminal sialic acid residue.

Purified capsular polysaccharides from *Streptococcus agalactiae* serotypes Ia, Ib and III were conjugated to a carrier protein by periodate oxidation followed by reductive amination. The carrier protein was CRM197.

Comparison of Purification by Ultrafiltration Versus Purification with Hydroxyapatite The conjugates were purified using either ultrafiltration (using tangential flow diafiltration with a 100 KDa membrane) or hydroxyapatite resin (both Type I or Type II 80 μm resins, Bio-Rad). Type I HA resin has a higher protein binding capacity and better capacity for acidic proteins, while Type II has a lower protein binding capacity but has better resolution of certain proteins. CRM197 has a molecular weight of around 60 KDa. While ultrafiltration using a 100 KDa membrane could separate conjugates of high molecular weight polysaccharides (such as serotype Ia conjugates of around 150 KDa, resulting in a total conjugate mass of around 210 KDa) from the conjugate/unconjugated CRM197 mixture, it could not be used for lower molecular weight conjugates (such as serotype III conjugates) which did not have a sufficient difference in molecular mass between the conjugated and unconjugated carrier protein.

In contrast, preliminary experiments showed that both Type I and Type II hydroxyapatite resin could be used to purify conjugated from unconjugated CRM197. The unconjugated CRM197 bound to the resin while the conjugated protein was protected by the conjugated saccharide and so was found in the flow through.

Testing Various Parameters for the Hydroxyapatite Purification pH

A pH of 6.8 is usually used for chromatography using hydroxyapatite. However, in this experiment a pH of 7.2 was used instead in order to ensure the stability of the saccharide. No effects on the efficiency of the chromatography were noticed due to this change in pH.

Phosphate Concentration

Different phosphate concentrations were tested to determine the effect on yield of purified conjugate. It was determined that CRM197 completely binds to the hydroxyapatite column if the phosphate concentration is ≤35 mM in the starting material and equilibration/post loading wash buffer (pH7.2). At these concentrations, CRM197-Ia/Ib conjugates were always completely recovered in the column flow through, while CRM197-III conjugates were recovered with a yield of 80-85%.

Wash Volume (After Loading)

Due to some interaction with the hydroxyapatite, not all the conjugates flowed immediately from the column during loading. However, it was found that at a phosphate concentration of 30 mM, all conjugates flowed through with less than 1.5 column volumes (CV) post-loading wash. Thus, loading volume was around 0.6 CV, the next 0.4 to 2.2 CV were collected and contained the conjugates.

Column Loading (Capacity)

At a phosphate concentration of 35 mM, it was found that hydroxyapatite was able to completely bind CRM197 at a ratio of total CRM:column volume of about <2.5 mg CRM per ml of resin. To reduce the chance of unconjugated CRM197 being present in the flow through, a lower CRM:column volume of about 1.5 mg CRM per ml of resin may be used.

Pilot Process

Following these experiments, a pilot process was set up using the following parameters:

Column volume=4 L (acceptable range: >3 L). Column selected had 20 cm diameter (corresponding height about 11±2.5 cm).

Column rinsing and equilibration: 5 CV of 400 mM sodium phosphate pH 6.8 buffer at 80 cm/h (419 ml/min) plus 5 CV of 35 mM sodium phosphate pH 7.2 buffer at 80 cm/h.

Column loading and product collection: load product (80 cm/h) and then wash with equilibration buffer; waste flow-through up to 0.4 CV, collect product up to 2.2 CV, then waste up to 2.9 CV.

Column eluted with 2 CV of 400 mM sodium phosphate pH 6.8 buffer at 80 cm/h to collect unconjugated CRM bound to the column (this fraction is not relevant for the process).

Comparison of Type I Hydroxyapatite with Type II Hydroxyapatite

Figure 5:
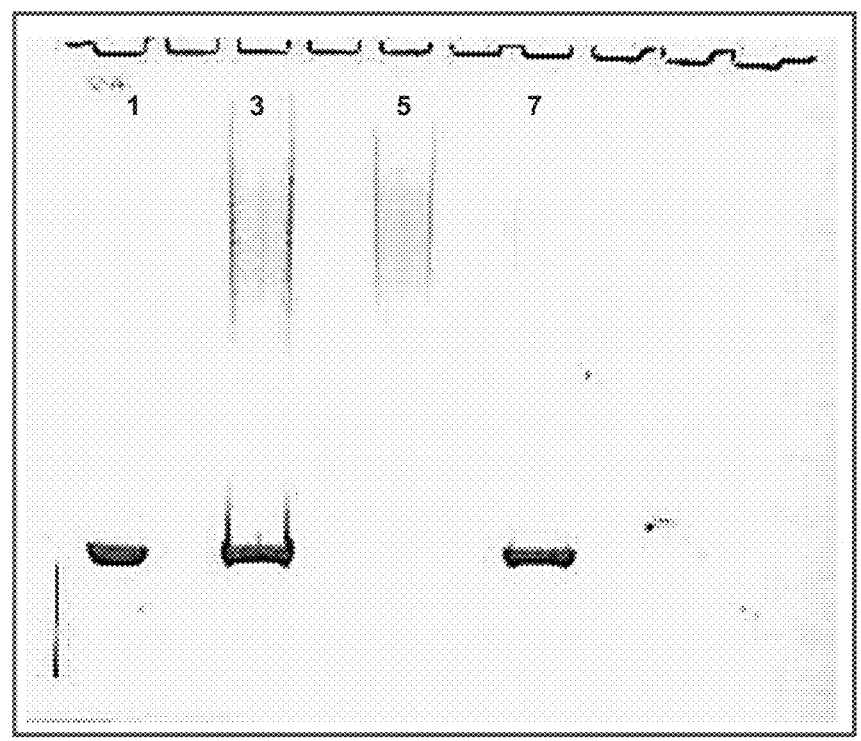
FIGS. 5 and 6 show SDS page of conjugate purification with type I and type II hydroxyapatite, respectively. Column key: 1-CRM, 3-Crude conjugate, 5-Flow through (conjugate), 7-Eluate (unconjugated CRM).
Figure 6:
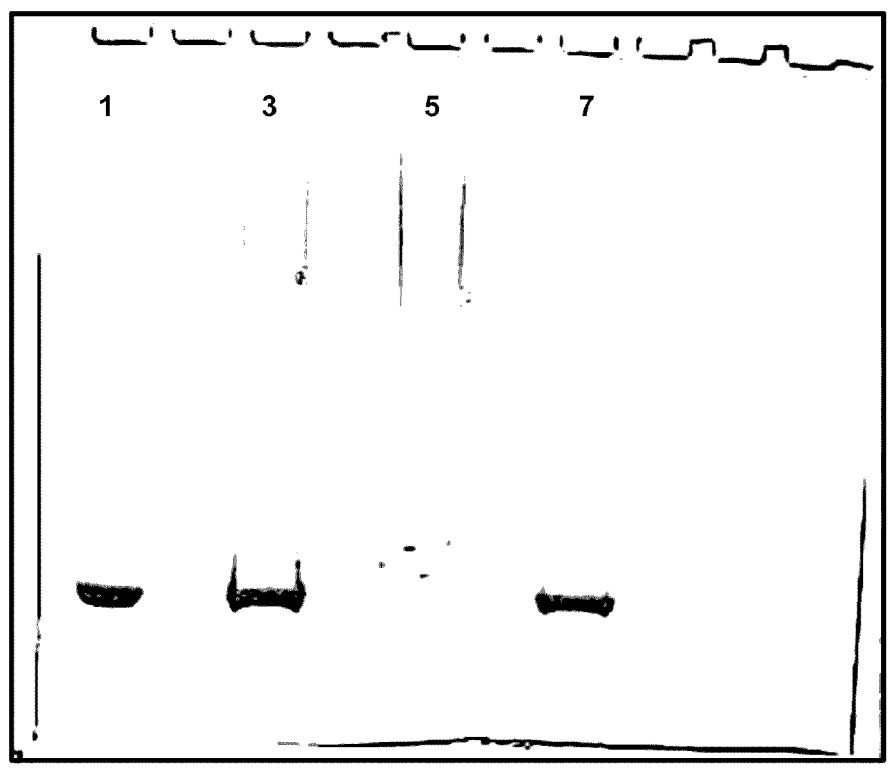
Figure 7:
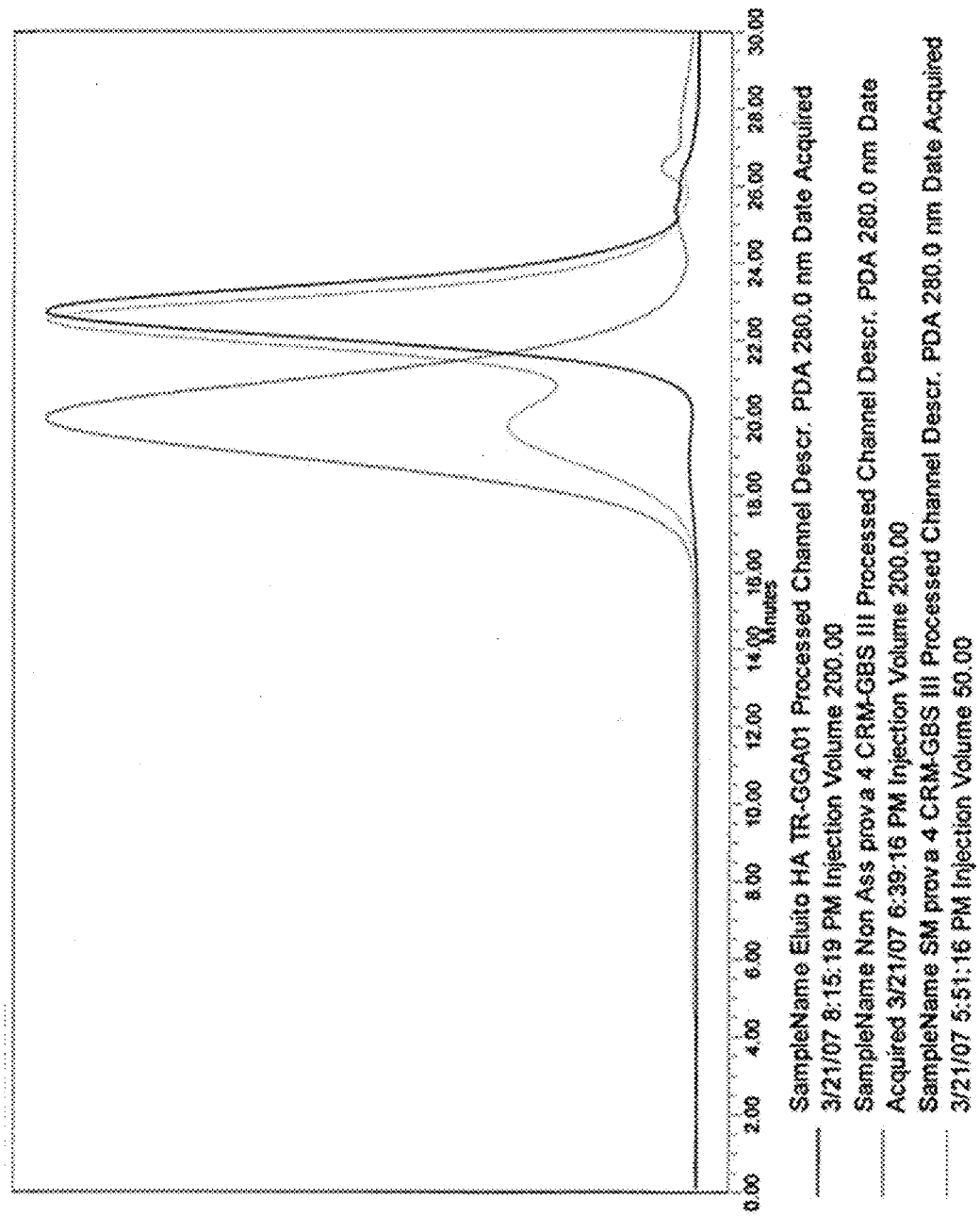
FIGS. 7 and 8 show HPLC output for type I and type II hydroxyapatite, respectively. The first peak is the conjugated CRM197-GBS Type III, the second peak is unconjugated CRM197.
Figure 8:
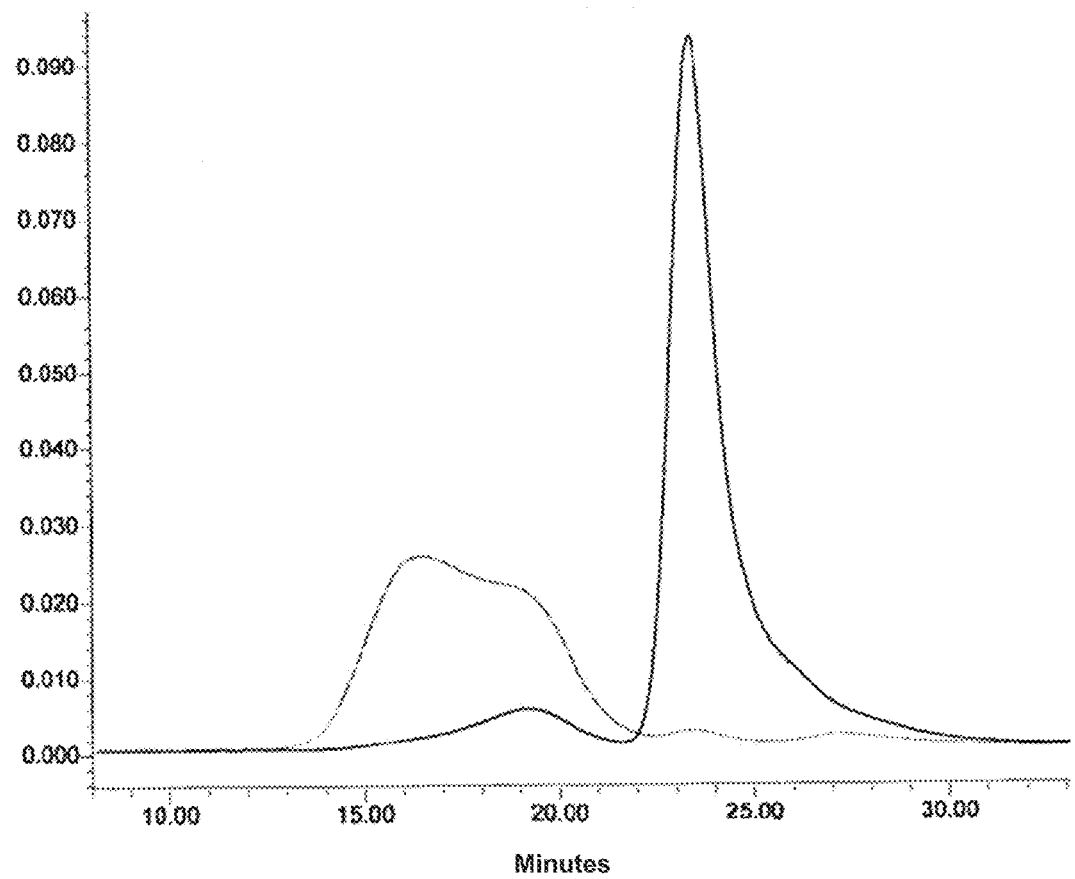

Type I and Type II hydroxyapatite were both found to purify the conjugate from the mixture with equal efficiency. FIGS. 5 and 6 show SDS page gels for Type I and Type II respectively. These gels clearly show that no unconjugated CRM197 was found in the flow through (lane 5). As expected, the unconjugated CRM197 was found in the eluate (lane 7). The starting material (mixture of conjugated and unconjugated CRM197), flow through and eluate was analysed by SE-HPLC. Two graphic displays of the HPLC process are seen in FIGS. 7 and 8 for Type I and Type II respectively. Each figure shows two distinct peaks that relate to the purified conjugate and the unconjugated CRM197. In FIG. 7, the double peak is the starting material, the first peak is the flow through (purified conjugate) and the second peak is the material eluted from the resin (unconjugated CRM197). In FIG. 8, the first peak is the flow through (purified conjugate) and the second peak is the material eluted from the resin (unconjugated CRM197).

Example 2

Conjugate Preparation

Purified, desialylated capsular polysaccharide from *Streptococcus agalactiae* serotype V was conjugated to a carrier protein by periodate oxidation followed by reductive amination. The carrier protein was CRM197.

Testing Column Loading Parameter for Hydroxyapatite Purification

Column Loading

At a phosphate concentration of 35 mM, it was found that hydroxyapatite was able to completely bind CRM197 at a ratio of total CRM:column volume of about <2.5 mg CRM per ml of resin. To reduce the chance of unconjugated CRM197 being present in the flow through, a lower CRM: column volume of about 1.5 mg CRM per ml of resin may be used.

Test Processes

Following this experiment, several test processes were set up using the following parameters:

| Parameter | Test 1 | Test 2 | Test 3 | Test 4 |
|---|---|---|---|---|
| Column height (cm) | 5.5 | 12 | 12.75 | 12.75 |
| Column diameter (cm) | 5 | 1.6 | 2.6 | 2.6 |
| Column volume (cm) | 108 | 24 | 68 | 68 |
| Loaded volume (ml) | 337 | 46 | 154 | 153 |
| Mass of CRM present in conjugation reaction/column volume (mg CRM per ml resin) | 5.0 | 3.5 | 3.6 | 3.5 |
| Flow through volume (ml) | 750 | 95 | 270 | 245 |
| Eluate volume (ml) | 125 | 28 | 100 | 104 |
| 0.2 μm filtration of eluate | No | Yes | Yes | Yes |

The test processes were analysed as follows:

| Parameter | Test 1 | Test 2 | Test 3 | Test 4 |
|---|---|---|---|---|
| Flow through protein concentration (μg/ml) | 564 | 691.1 | 755 | 789 |
| Eluate protein concentration (μg/ml) | 816 | 474.4 | 342 | 245 |
| Flow through saccharide concentration (μg/ml) | not detected | 832.52 | 1067.09 | 1166.29 |
| Eluate saccharide concentration (μg/ml) | not detected | 159.78 | 92.35 | 65.35 |
| Estimation of % conjugate in eluate (% total proteins) | 11.2 | not detected | 8.57 | 6.35 |
| Unconjugated CRM in flow through (% total proteins) | 16% | not detected | not detectable | not detectable |

The yields from the test processes were measured as follows:

| Parameter | Test 1 | Test 2 | Test 3 | Test 4 |
|---|---|---|---|---|
| Unconjugated CRM estimated in crude (% by SE-HPLC) | 29.5 | 15.1 | 11.3 | 8.9 |
| Protein recovery in flow through (% of CRM present in conjugation reaction) | 78.3 | 77.8 | 84.5 | 68.2 |
| Protein recovery in eluate (% of CRM present in conjugation reaction) | 18.9 | 24.8 | 14.2 | 9.0 |
| Saccharide recovery in flow through (% of saccharide present in conjugation reaction) | not detected | 81.7 | 90.2 | 96.4 |
| Saccharide recovery in eluate (% of saccharide present in conjugation reaction) | not detected | 5.8 | 2.9 | 2.3 |

These data show that hydroxyapatite chromatography allows recovery of more than 90% of desialylated GBS type V capsular polysaccharide conjugated to CRM197 from the mixture. Although the test runs gave values around 80%, these values are relative to the total amount of CRM197 that was present in the conjugation reaction, 10-25% of which would have remained unconjugated prior to loading on the hydroxyapatite resin.

The starting material (mixture of conjugated and unconjugated CRM197), flow through and eluate was analysed by SE-HPLC. As for the GBS type Ia, Ib and III conjugates discussed above, distinct peaks were seen relating to the purified conjugate and the unconjugated CRM197. This result shows that hydroxyapatite chromatography allows essentially complete removal of unconjugated CRM197 from the conjugate.

It will be understood that the invention has been described by way of example only and modifications may be made whilst remaining within the scope and spirit of the invention.

REFERENCES

[1] Peltola (2000) *Clin Microbiol Rev* 13:302-317
[2] Wuorimaa & Kayhty (2002) *Scand J Immunol* 56:111-129
[3] Balmer et al. (2002) *J Med Microbiol* 51:717-722
[4] Alexander et al. (2000) J Immunol 164:1625-1633
[5] WO99/55730
[6] Lei et al. (2000) *Dev Biol (Basel)* 103:259-264.
[7] WO00/38711; U.S. Pat. No. 6,146,902.
[8] WO94/06467.
[9] Anonymous (January 2002) *Research Disclosure*, 453077.
[10] Anderson (1983) *Infect Immun* 39(1):233-238.
[11] Anderson et al. (1985) *J Clin Invest* 76(1):52-59.
[12] EP-A-0372501.
[13] EP-A-0378881.
[14] EP-A-0427347.
[15] WO93/17712
[16] WO94/03208.
[17] WO98/58668.
[18] EP-A-0471177.
[19] WO91/01146
[20] Falugi et al. (2001) *Eur J Immunol* 31:3816-3824.
[21] Baraldo et al. (2004) *Infect Immun* 72(8):4884-7.
[22] EP-A-0594610.
[23] Ruan et al. (1990) *J Immunol* 145:3379-3384.
[24] WO00/56360.
[25] Kuo et al. (1995) *Infect Immun* 63:2706-13.
[26] WO02/091998.
[27] WO01/72337
[28] WO00/61761.
[29] WO02/34771
[30] WO03/093306
[31] WO04/041157
[32] WO2005002619
[33] WO2005/033148
[34] WO2006/067632
[35] WO03/007985
[36] *Vaccine* (ed Plotkin et al) Fourth Edition ISBN 0-7216-9688-0
[37] Wessels et al. (1990) *J Clin Invest* 86:1428-33.
[38] Wessels et al. (1989) *Infect Immun* 57:1089-94.
[39] WO2006/082527
[40] U.S. patent application 61/008,941, entitled "FERMENTATION PROCESSES FOR CULTIVATING STREPTOCOCCI AND PURIFICATION PROCESSES FOR OBTAINING CPS THEREFROM" filed on 20 Dec. 2007.
[41] WO03/080678
[42] WO2006/050341
[43] Ravenscroft et al. (1999) *Vaccine* 17:2802-2816.
[44] Costantino et al. (1999) *Vaccine* 17:1251-1263.
[45] WO2007/000341.
[46] Lees et al. (1996) *Vaccine* 14:190-198.

[47] WO95/08348.
[48] WO98/42721
[49] U.S. Pat. No. 4,356,170.
[50] WO2006/082530.
[51] WO2007/000342.
[52] U.S. Pat. No. 4,882,317
[53] U.S. Pat. No. 4,695,624
[54] *Mol. Immunol.,* 1985, 22, 907-919
[55] EP-A-0208375
[56] WO00/10599
[57] Gever et al., Med. Microbiol. Immunol, 165: 171-288 (1979).
[58] U.S. Pat. No. 4,057,685.
[59] U.S. Pat. Nos. 4,673,574; 4,761,283; 4,808,700.
[60] U.S. Pat. No. 4,459,286.
[61] U.S. Pat. No. 4,965,338
[62] U.S. Pat. No. 4,663,160.
[63] U.S. Pat. No. 4,761,283
[64] U.S. Pat. No. 4,356,170
[65] Lei et al. (2000) *Dev Biol (Basel)* 103:259-264.
[66] WO00/38711; U.S. Pat. No. 6,146,902.
[67] WO99/24578
[68] WO99/36544
[69] WO99/57280
[70] WO00/22430.
[71] Tettelin et al. (2000) Science 287:1809-1815
[72] WO96/29412
[73] Pizza et al. (2000) Science 287:1816-1820
[74] WO01/52885
[75] Bjune et al. (1991) *Lancet* 338(8775):1093-96
[76] Fukasawa et al. (1999) *Vaccine* 17:2951-2958.
[77] Rosenqvist et al. (1998) *Dev. Biol. Stand.* 92:323-333.
[78] Costantino et al. (1992) *Vaccine* 10:691-698.
[79] Costantino et al. (1999) *Vaccine* 17:1251-1263.
[80] WO03/007985.
[81] WO00/66791
[82] WO01/64922
[83] WO01/64920
[84] WO03/020756
[85] WO2004/032958
[86] WO2004/048404.
[87] WO98/18931
[88] WO98/18930
[89] U.S. Pat. No. 6,699,703
[90] U.S. Pat. No. 6,800,744
[91] WO97/43303
[92] WO97/37026
[93] Watson (2000) *Pediatr Infect Dis J* 19:331-332.
[94] Rubin (2000) *Pediatr Clin North Am* 47:269-285, v.
[95] Jedrzejas (2001) *Microbiol Mol Biol Rev* 65:187-207.
[96] WO02/22167.
[97] Paoletti et al., (1990) *J Biol Chem* 265:18278-83.
[98] Wessels et al., (1990) *J Clin Invest* 86:1428-33.
[99] Baker et al., (2004) *J Infect Dis* 171:879-84.
[100] WO02/34771
[101] WO2005/032582
[102] WO02/094851
[103] Dale, Vaccine (1999) 17:193-200
[104] Dale, Vaccine 14(10): 944-948
[105] Dale (1999) *Infect Dis Clin North Am* 13:227-43, viii.
[106] Ferretti et al. (2001) *PNAS USA* 98: 4658-4663.
[107] WO02/18595
[108] WO99/58562
[109] McMichael (2000) *Vaccine* 19 Suppl 1:S101-107.
[110] Gustafsson et al. (1996) *N. Engl. J. Med.* 334:349-355.
[111] Rappuoli et al. (1991) *TIBTECH* 9:232-238.
[112] Kuroda et al. (2001) *Lancet* 357(9264):1225-1240; see also pages 1218-1219.
[113] WO03/093306
[114] Schuchat (1999) Lancer 353(9146):51-6
[115] WO2004/041157
[116] WO2005/002619
[117] Zhu et al., Vaccine (2004) 22:660-669
[118] Price et al., Infection and Immunity (2004) 71(1):277-283)
[119] Plante et al., J Infectious Disease (2000) 182:848-855)
[120] WO02/079243
[121] WO00/37494
[122] WO03/049762
[123] WO03/068811
[124] WO99/28475.
[125] Anderson (2000) *Vaccine* 19 Suppl 1:S59-65.
[126] Kahn (2000) *Curr Opin Pediatr* 12:257-262.
[127] Crowe (1995) *Vaccine* 13:415-421.
[128] *J Gen Virol.* 2004 November; 85(Pt 11):3229
[129] Bell (2000) *Pediatr Infect Dis J* 19:1187-1188.
[130] Iwarson (1995) *APMIS* 103:321-326.
[131] Gerlich et al. (1990) *Vaccine* 8 Suppl:S63-68 & 79-80.
[132] WO98/20734.
[133] WO03/009869
[134] WO01/30390.
[135] *Vaccine Design* . . . (1995) eds. Powell & Newman. ISBN: 030644867X. Plenum.
[136] WO00/23105.
[137] WO90/14837.
[138] Podda (2001) *Vaccine* 19:2673-80.
[139] Frey et al. (2003) *Vaccine* 21:4234-7.
[140] U.S. Pat. No. 6,299,884.
[141] U.S. Pat. No. 6,451,325.
[142] Allison & Byars (1992) *Res Immunol* 143:519-25.
[143] Hariharan et al. (1995) *Cancer Res* 55:3486-9.
[144] U.S. Pat. No. 5,057,540.
[145] WO96/33739.
[146] EP-A-0109942.
[147] WO96/11711.
[148] WO00/07621.
[149] Barr et al. (1998) *Advanced Drug Delivery Reviews* 32:247-271.
[150] Sjolanderet et al. (1998) *Advanced Drug Delivery Reviews* 32:321-338.
[151] Niikura et al. (2002) *Virology* 293:273-280.
[152] Lenz et al. (2001) *J Immunol* 166:5346-5355.
[153] Pinto et al. (2003) *J Infect Dis* 188:327-338.
[154] Gerber et al. (2001) *Virol* 75:4752-4760.
[155] WO03/024480
[156] WO03/024481
[157] Gluck et al. (2002) *Vaccine* 20:B10-B16.
[158] EP-A-0689454.
[159] Johnson et al. (1999) *Bioorg Med Chem Lett* 9:2273-2278.
[160] Evans et al. (2003) *Expert Rev Vaccines* 2:219-229.
[161] Meraldi et al. (2003) *Vaccine* 21:2485-2491.
[162] Pajak et al. (2003) *Vaccine* 21:836-842.
[163] Kandimalla et al. (2003) *Nucleic Acids Research* 31:2393-2400.
[164] WO02/26757.
[165] WO99/62923.
[166] Krieg (2003) *Nature Medicine* 9:831-835.
[167] McCluskie et al. (2002) *FEMS Immunology and Medical Microbiology* 32:179-185.
[168] WO98/40100.
[169] U.S. Pat. No. 6,207,646.
[170] U.S. Pat. No. 6,239,116.

[171] U.S. Pat. No. 6,429,199.
[172] Kandimalla et al. (2003) *Biochemical Society Transactions* 31 (part 3):654-658.
[173] Blackwell et al. (2003) *J Immunol* 170:4061-4068.
[174] Krieg (2002) *Trends Immunol* 23:64-65.
[175] WO01/95935.
[176] Kandimalla et al. (2003) *BBRC* 306:948-953.
[177] Bhagat et al. (2003) *BBRC* 300:853-861.
[178] WO03/035836.
[179] WO95/17211.
[180] WO98/42375.
[181] Beignon et al. (2002) *Infect Immun* 70:3012-3019.
[182] Pizza et al. (2001) *Vaccine* 19:2534-2541.
[183] Pizza et al. (2000) *Int J Med Microbiol* 290:455-461.
[184] Scharton-Kersten et al. (2000) *Infect Immun* 68:5306-5313.
[185] Ryan et al. (1999) *Infect Immun* 67:6270-6280.
[186] Partidos et al. (1999) *Immunol Lett* 67:209-216.
[187] Peppoloni et al. (2003) *Expert Rev Vaccines* 2:285-293.
[188] Pine et al. (2002) *J Control Release* 85:263-270.
[189] Domenighini et al. (1995) *Mol Microbiol* 15:1165-1167.
[190] WO03/011223.
[191] WO99/40936.
[192] Matsui M. et al. (2004) J. Virol 78: 9093.
[193] WO99/44636.
[194] Lillard J W et al., (2003) *Blood* February 1; 101(3):807-14. Epub 2002 Sep. 12.
[195] Singh et al] (2001) *J Cont Release* 70:267-276.
[196] WO99/27960.
[197] U.S. Pat. No. 6,090,406
[198] U.S. Pat. No. 5,916,588
[199] EP-A-0626169.
[200] WO99/52549.
[201] WO01/21207.
[202] WO01/21152.
[203] Andrianov et al. (1998) *Biomaterials* 19:109-115.
[204] Payne et al. (1998) *Adv Drug Delivery Review* 31:185-196.
[205] Stanley (2002) *Clin Exp Dermatol* 27:571-577.
[206] Jones (2003) *Curr Opin Investig Drugs* 4:214-218.
[207] WO04/60308
[208] WO04/64759.
[209] U.S. Pat. No. 6,924,271.
[210] US2005/0070556.
[211] U.S. Pat. No. 5,658,731.
[212] Wong et al. (2003) *J Clin Pharmacol* 43(7):735-42.
[213] US2005/0215517.
[214] WO02/072012.
[215] *Vaccine Adjuvants: Preparation Methods and Research Protocols* (Volume 42 of *Methods in Molecular Medicine* series). ISBN: 1-59259-083-7. Ed. O'Hagan.
[216] Signorelli & Hadden (2003) *Int Immunopharmacol* 3(8):1177-86.
[217] WO2004/064715.
[218] Cooper (1995) *Pharm Biotechnol* 6:559-80.
[219] WO2006/002422.
[220] WO2004/87153.
[221] U.S. Pat. No. 6,605,617.
[222] WO02/18383.
[223] WO2004/018455.
[224] WO03/082272.
[225] U.S. Pat. No. 5,011,828.
[226] U.S. Pat. No. 6,586,409.
[227] WO99/11241.
[228] WO94/00153.
[229] WO98/57659.
[230] European patent applications 0835318, 0735898 and 0761231.

The invention claimed is:

1. A method of separating capsular saccharide antigen conjugated to a carrier protein from the carrier protein not conjugated to the capsular saccharide antigen in a mixture comprising the carrier protein not conjugated to the capsular saccharide antigen and the capsular saccharide antigen conjugated to the carrier protein, wherein the capsular saccharide antigen conjugated to the carrier protein is from *N. meningitidis, S. pneumoniae, S. pyogenes, S. agalactiae, H. influenzae, P. aeruginosa, S. aureus, E. faecalis, E. faecium, V. cholerae,* or *S. typhi,* comprising
contacting said mixture with hydroxyapatite under conditions that allow the binding of the carrier protein not conjugated to the capsular saccharide antigen to the hydroxyapatite, and wherein the capsular saccharide antigen conjugated to the carrier protein does not bind to the hydroxyapatite; and
collecting the capsular saccharide antigen conjugated to the carrier protein unbound to the hydroxyapatite.

2. The method of claim 1, wherein the mixture further comprises other contaminant proteins.

3. The method of claim 1 or claim 2, wherein the carrier protein is selected from tetanus toxoid, diphtheria toxoid or $CRM_{197}$, *N. meningitidis* outer membrane proteins, synthetic proteins, heat shock proteins, pertussis proteins, cytokines, lymphokines, hormones, growth factors, protein D of *H. influenzae*, pneumolysin, pneumococcal surface protein PspA, iron uptake proteins, toxin A or toxin B of *C. difficile* and a polyepitope carrier.

4. The method of claim 1 or claim 2, wherein said carrier protein is tetanus toxoid, or diphtheria toxoid or $CRM_{197}$.

5. The method of claim 1, wherein said carrier protein is $CRM_{197}$.

6. The method of claim 1 wherein the capsular saccharide antigen has a molecular weight of 5 kDa or more.

7. The method of claim 6, wherein the capsular saccharide antigen has a molecular weight of 50 kDa or more.

8. The method of claim 1 wherein the capsular saccharide antigen is glycosylated.

9. The method of claim 1, wherein the capsular saccharide antigen is conjugated to the carrier protein by a linker.

10. The method of claim 1, wherein said method is carried out at pH 6.5-pH 7.5.

11. The method of claim 1 wherein said method is carried out at pH 7.2.

12. The method of claim 1 wherein said method is carried out at a phosphate concentration of 50 mM or less.

13. The method of claim 1 wherein said hydroxyapatite is in the form of a gel.

14. The method of claim 1 wherein said hydroxyapatite has a particle size of 40 µm or more.

15. The method of claim 1 wherein said hydroxyapatite has a dynamic binding capacity of >10 mg lysozyme per gram.

16. A method of preparing a composition comprising the method of claim 1, and further comprising mixing said capsular saccharide antigen conjugated to the carrier protein unbound to the hydroxyapatite with a pharmaceutically acceptable diluent or carrier thereby preparing the pharmaceutical composition.

17. The method of claim 16, further comprising mixing the composition with an adjuvant.

* * * * *

UNITED STATES PATENT AND TRADEMARK OFFICE
CERTIFICATE OF CORRECTION

PATENT NO.       : 9,463,250 B2                                                    Page 1 of 1
APPLICATION NO.  : 12/669464
DATED            : October 11, 2016
INVENTOR(S)      : Bigio et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 798 days.

Signed and Sealed this
Twenty-fifth Day of September, 2018

Andrei Iancu
*Director of the United States Patent and Trademark Office*